US012334221B2

(12) United States Patent
Rohde et al.

(10) Patent No.: US 12,334,221 B2
(45) Date of Patent: Jun. 17, 2025

(54) SYSTEM, METHOD AND COMPUTER READABLE MEDIUM FOR VIDEO-BASED FACIAL WEAKNESS ANALYSIS FOR DETECTING NEUROLOGICAL DEFICITS

(71) Applicant: University of Virginia Patent Foundation, Charlottesville, VA (US)

(72) Inventors: Gustavo Rohde, Dunn Loring, VA (US); Andrew M. Southerland, Charlottesville, VA (US); Yan Zhuang, Charlottesville, VA (US); Mark McDonald, Charlottesville, VA (US); Omar Uribe, Sterling, VA (US); Chad M. Aldridge, Charlottesville, VA (US); Mohamed Abul Hassan, Davis, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 509 days.

(21) Appl. No.: 17/665,334

(22) Filed: Feb. 4, 2022

(65) Prior Publication Data
US 2022/0319707 A1  Oct. 6, 2022

Related U.S. Application Data

(60) Provisional application No. 63/146,220, filed on Feb. 5, 2021.

(51) Int. Cl.
| | | |
|---|---|---|
| *G06V 10/00* | (2022.01) | |
| *G16H 30/20* | (2018.01) | |
| *G16H 50/20* | (2018.01) | |

(52) U.S. Cl.
CPC .............. *G16H 50/20* (2018.01); *G16H 30/20* (2018.01)

(58) Field of Classification Search
CPC ........ G16H 50/20; G16H 30/20; G16H 30/40; G16H 40/63; G16H 50/30; G16H 50/70
See application file for complete search history.

(56) References Cited

U.S. PATENT DOCUMENTS

| | | |
|---|---|---|
| 10,846,370 B2 | 11/2020 | Southerland et al. |
| 11,540,749 B2 | 1/2023 | Uribe et al. |
| | (Continued) | |

FOREIGN PATENT DOCUMENTS

| | | |
|---|---|---|
| WO | 2015/026808 A1 | 2/2015 |
| WO | 2019/144141 A1 | 7/2019 |

OTHER PUBLICATIONS

Prediction of Alzheimer's Disease Based on Bidirectional LSTM Qiao Pan et al 2019 J. Phys.: Conf. Ser. 1187 052030 (Year: 2019).*

(Continued)

*Primary Examiner* — Vu Le
*Assistant Examiner* — Zaid Muhammad Saleh
(74) *Attorney, Agent, or Firm* — Robert J. Decker

(57) ABSTRACT

An automated and quantitative facial weakness screening framework that utilizes a Bi-LSTM network to model the temporal dynamics among the shape and appearance features. The technique is beneficial to assist the paramedics or other users to identify the facial weakness in the field or, more importantly, whenever expertise in neurology is not available either for emergency patient triage (e.g., pre-hospital stroke care) or chronic disease management (e.g., Bell's palsy rehabilitation screen), leading to increased coverage and earlier treatment. The technique provides visualizable and interpretable results to increase its transparency and interpretability. The technique provides for inexpensive solutions that can be used in areas underserved (Continued)

by non-neurologists to more readily identify neurological deficits such as facial weakness in the field or other environment.

39 Claims, 14 Drawing Sheets

(56) References Cited

U.S. PATENT DOCUMENTS

| | | | |
|---|---|---|---|
| 2004/0175020 | A1* | 9/2004 | Bradski ................ G06F 1/3203 382/103 |
| 2011/0218253 | A1 | 9/2011 | Lange et al. |
| 2011/0310237 | A1* | 12/2011 | Wang ...................... H04N 7/18 382/190 |
| 2014/0028669 | A1* | 1/2014 | Tsukagoshi .......... H04N 13/279 345/419 |
| 2015/0112232 | A1 | 4/2015 | Quatieri et al. |
| 2016/0275376 | A1* | 9/2016 | Kant ................... G06F 18/2415 |
| 2017/0007167 | A1* | 1/2017 | Kostic ................. A61B 5/6898 |
| 2017/0046569 | A1 | 2/2017 | Rao et al. |
| 2019/0110754 | A1* | 4/2019 | Rao ......................... G06N 7/00 |
| 2019/0172458 | A1* | 6/2019 | Mishra ................... G06V 10/82 |

OTHER PUBLICATIONS

W. Hong, D. Wei and A. U. Batur, "Video stabilization and rolling shutter distortion reduction," 2010 IEEE International Conference on Image Processing, Hong Kong, China, 2010, pp. 3501-3504, doi: 10.1109/ICIP.2010.5649595. (Year: 2010).*
Patel, Donika et al., "Bell palsy: Clinical examination and management," Cleveland Clinic Journal of Medicine, vol. 82, No. 7, Jul. 2015, pp. 419-426.
Yew, Kenneth et al., "Acute stroke diagnosis," Am Fam Physician, vol. 80, No. 1, Jul. 1, 2009, pp. 33-40.
Nor, Mohd et al., "Agreement between ambulance paramedic-and physician-recorded neurological signs with face arm speech test (FAST) in acute stroke patients," Stroke, vol. 35, No. 6, Jun. 2004, pp. 1355-1359.
Hansen, M. et al., "Interobserver variation in the evaluation of neurological signs: observer dependent factors," Acta Neurologica Scandinavica, vol. 90, No. 3, 1994, pp. 145-149.
Powers, William J. et al., "2015 American Heart Association/American Stroke Association focused update of the 2013 guidelines for the early management of patients with acute ischemic stroke regarding endovascular treatment," Stroke, vol. 46, No. 10, Oct. 2015, pp. 3020-3035.
Reitzen, Shari et al., "Significance and reliability of the House-Brackmann grading system for regional facial nerve function," Otolaryngol Head Neck Surg, vol. 140, No. 2, Feb. 2009, pp. 154-158.
Mosley, Ian et al., "The impact of ambulance practice on acute stroke care," Stroke, vol. 38, No. 10, Oct. 2007, pp. 2765-2770.
Adams, Harold P. et al., "Guidelines for the early management of adults withischemic stroke," Stroke, vol. 38, No. 5, May 2007, pp. 1655-1711.
Glober, Nancy K. et al., "Acute stroke: Current evidence-based recommendations for prehospital care," Western Journal of Emergency Medicine, vol. 17, No. 2, Mar. 2, 2016, pp. 104-128.
Sacco, Ralph L., "Neurology: Challenges, opportunities, and the way forward," Neurology, vol. 93, No. 21, Nov. 19, 2019, pp. 911-918.
Moulin, Thierry et al., "Telemedicine in stroke: Potentials, limitations and ongoing issues," Advances in Telemedicine: Applications in Various Medical Disciplines and Geographical Regions, Mar. 22, 2011, pp. 3-28 (27 pages total).
Lecun, Yann et al., "Deep Learning," Nature, vol. 521, May 28, 2015, pp. 436-444.
Thevenot, Jerome et al., "A survey on computer vision for assistive medical diagnosis from faces," IEEE.

Linstrom, Christopher et al., "Facial-motion analysis with a video and computer system: a preliminary report," The American Journal of Otology, vol. 21, No. 1, Jan. 2000, pp. 123-129.
Ko, Byoung Chul, "A brief review of facial emotion recognition based on visual information," Sensors, vol. 18, No. 2, Published Jan. 30, 2018, pp. 401-420.
Anping, Song et al., "Assessment for facial nerve paralysis based on facial asymmetry," Australasian Physical and Engineering Sciences in Medicine, vol. 40, No. 4, Oct. 25, 2017, pp. 851-860.
Zhuang, Yan et al., "Pathological facial weakness detection using computational image analysis," 2018 IEEE 15th International Symposium on Biomedical Imaging (ISBI 2018), Apr. 4-7, 2018, pp. 261-264.
Guo, Zhexiao et al., "An unobtrusive computerized assessment framework for unilateral peripheral facial paralysis," IEEE Journal of Biomedical and Health Informatics, vol. 22, No. 3, May 2018, pp. 835-841.
Zhuang, Yan et al., "Facial weakness analysis and quantification of static images", IEEE Journal of Biomedical and Health Informatics, vol. 24, No. 8, Aug. 2020, pp. 2260-2267.
Guo, Zhexiao et al., "Deep assessment process: Objective assessment process for unilateral peripheral facial paralysis via deep convolutional neural network", IEEE 14th International Symposium on Biomedical Imaging, 2017, pp. 135-138.
Haase, Daniel et al., "Automated and objective action coding of facial expressions in patients with acute facial palsy", European Archives of Oto-Rhino-Laryngology, vol. 272, No. 5, 2015, pp. 1259-1267.
Modersohn, Luise et al., "Facial paresis index prediction by exploiting active appearance models for compact discriminative features", International Conference on Computer Vision Theory and Applications (vol. 4 VISAPP), 2016. pp. 271-278.
Kim, Hyun Seok, et al., "A smartphone-based automatic diagnosis system for facial nerve palsy", Sensors, vol. 15, No. 10, 2015, pp. 26756-26768.
Wang, Ting et al., "Automatic evaluation of the degree of facial nerve paralysis", Multimedia Tools and Applications, vol. 75, 2016, pp. 11893-11908.
Gaber, Amira et al., "Quantifying facial paralysis using the kinect v2", 37th Annual International Conference of the IEEE Engineering in Medicine and Biology Society, 2015, pp. 2497-2501.
He, Shu et al., "Quantitative analysis of facial paralysis using local binary patterns in biomedical videos", IEEE Transactions on Biomedical Engineering, vol. 56, No. 7, Jul. 2009, pp. 1864-1870.
He, Shu et al., "Biomedical image sequence analysis with application to automatic quantitative assessment of facial paralysis", EURASIP Journal on Image and Video Processing, vol. 2007, 2011, pp. 1-11.
Li, Pengfei et al, "A two-stage method for assessing facial paralysis severity by fusing multiple classifiers", 14th Chinese Conference Biometric Recognition, 2019, pp. 231-239.
Zhuang, Yan et al., "F-DIT-V: An automated video classification tool for facial weakness detection", IEEE EMBS International Conference on Biomedical & Health Informatics, 2019, pp. 1-4.
Xu, Pengfei et al., "Automatic evaluation of facial nerve paralysis by dual-path LSTM with deep differentiated network", Neurocomputing, vol. 388, 2020, pp. 70-77, DOI: 10. HH6/i.neucom.2020.01.014.
Storey, Gary et al., "3DPalsyNet: A facial palsy grading and motion recognition framework using fully 3D convolutional neural networks", IEEE Access, vol. 7, 2019, pp. 121655-121664.
Bandini, Andrea et al., "Automatic detection of amyotrophic lateral sclerosis (ALS) from video-based analysis of facial movements: speech and non-speech tasks", 13th IEEE International Conference on Automatic Face & Gesture Recognition, 2018, pp. 150-157.
Alagha, Mahmoud Amir et al., "Reproducibility of the dynamics of facial expressions in unilateral facial palsy", International Journal of Oral and Maxillofacial Surgery, vol. 47, No. 2, 2018, pp. 268-275.
Desrosiers, Paul Audain et al, "Analyzing of facial paralysis by shape analysis of 3D face sequences", Image and Vision Computing, vol. 67, 2017, pp. 67-88.
Felzenszwalb, Pedro et al., "Object detection with discriminatively trained part-based models", IEEE Transactions on Pattern Analysis and Machine Intelligence, vol. 32, No. 9, Sep. 2010, pp. 1627-1645.

(56) References Cited

OTHER PUBLICATIONS

Gower, J., "Generalized Procrustes Analysis", Psychometrika, vol. 40, No. 1, 1975, pp. 33-51.

Irani, Michal, "Multi-frame optical flow estimation using subspace constraints", Proceedings of the 7th IEEE International Conference on Computer Vision, 1999. pp. 626-633.

Abdi, Hervé et al., "Principal component analysis", Wiley interdisciplinary reviews: computational statistics, vol. 2, No. 4, 2010, pp. 433-459.

Wang, Wei et al., "Penalized fisher discriminant analysis and its application to image-based morphometry", Pattern Recognition Letters, vol. 32, No. 15, 2011, pp. 2128-2135.

Goodfellow, I. et al., "Deep Learning", Cambridge, MA, USA: MIT press Cambridge, vol. 1, 2016.

Adams, H. et al., "Baseline NIH Stroke Scale score strongly predicts outcome after stroke: a report of the Trial of Org 10172 in Acute Stroke Treatment (TOAST)", Neurology, vol. 53, No. 1, 1999, pp. 126-126.

Kazemi, Vahid et al., "One millisecond face alignment with an ensemble of regression trees", Proceedings of the IEEE Conference on Computer Vision and Pattern Recognition, 2014, pp. 1867-1874.

Chrysos, Grigorios G. et al. "A comprehensive performance evaluation of deformable face tracking in-the-wild". International Journal of Computer Vision, vol. 126, No. 2-4, 2018, pp. 198-232.

Donahue, Jeffrey et al., "Long-term recurrent convolutional networks for visual recognition and description", Proceedings of the IEEE Conference on Computer Vision and Pattern Recognition, 2015, pp. 2625-2634.

Ma, Chih-Yao et al., "TS-LSTM and temporal-inception: Exploiting spatiotemporal dynamics for activity recognition", Signal Processing: Image Communication, vol. 71, 2019, pp. 76-87.

Dietterich, Thomas., "Approximate statistical tests for comparing supervised classification learning algorithrns," Neural Computation, vol. 10, No. 7, 1998, pp. 1895-1923.

Raschka, Sebastian, "MIxtend: Providing machine learning and data science utilities and extensions to Python's scientific computing stack", Journal of Open Source Software, vol. 3, No. 24, 2018, pp. 638-640.

Nag, Sauradip et al., "Facial micro-expression spotting and recognition using time contrasted feature with visual memory", ICASSP IEEE International Conference on Acoustics, Speech and Signal Processing, 2019, pp. 2022-2026.

Maheswaranathan, Niru et al., "Reverse engineering recurrent networks for sentiment classification reveals line attractor dynamics", Advances in Neural Information Processing Systems, 2019, pp. 1596-15705.

Logitech, "C920 technical specifications," Jan. 2013, [Online], Available: https://support.logi.corn/hc/en-us/articles/360023307294-C920-TechnicalSpecifications.

Greenspan, Hayit et al., "Guest editorial deep learning in medical imaging: Overview and future promise of an exciting new technique", IEEE Transactions on Medical Imaging, vol. 35, No. 5, May 2016, pp. 1153-1159.

Esteva, Andre et al., "A guide to deep learning in healthcare", Nature Medicine, vol. 25, No. 1, Jan. 2019 (Published online Jan. 7, 2019), pp. 24-29.

Li, Shan et al., "Deep facial expression recognition: A survey", IEEE Transactions on Affective Computing, 2020, pp. 1-25.

Simonyan, Karen et al., "Two-stream convolutional networks for action recognition in videos", Advances in Neural Information Processing Systems, vol. 27, 2014, pp. 1-11.

Zhuang, Yan et al., "Video-based facial weakness analysis", IEEE Transactions on Biomedical Engineering, vol. 68, No. 9, Sep. 2021 (Date of Publication Jan. 6, 2021), pp. 2698-2705.

\* cited by examiner

Shape-based Features

Appearance-based Features

Full Face

SYSTEM, METHOD AND COMPUTER READABLE MEDIUM FOR VIDEO-BASED FACIAL WEAKNESS ANALYSIS FOR DETECTING NEUROLOGICAL DEFICITS

CROSS REFERENCE TO RELATED APPLICATIONS

The present application claims benefit of priority under 35 U.S.C § 119 (e) from U.S. Provisional Application Ser. No. 63/146,220, filed Feb. 5, 2021, entitled "System and Method for Providing Facial Weakness Analysis"; the disclosure of which is hereby incorporated by reference herein in its entirety.

FIELD OF INVENTION

The present disclosure relates generally to analyzing facial weakness using a camera and detecting neurological deficits using an algorithm based on the facial analysis information.

BACKGROUND

The configuration and movement of the face can indicate the presence or absence of various neurological diseases, such as Bell's palsy and stroke [1], [2]. However, recognizing the signs of neurological deficits such as facial weakness still remains as a challenge, because it requires neurological training and experience [3], [4]. In pre-hospital stroke and Bell's palsy care, several pen-and-paper style checklist based screening instruments have been developed to standardize instructions and exam procedures for identifying facial weakness [5], [6]. However, without proper training and experience in neurology, the accuracy and reliability of these instruments are limited and the interpretation is highly subjective for non-neurologist providers such as EMS personnel [7], [8]. For instance, one study showed that paramedics failed to identify 15% of patients with facial weakness and erroneously interpreted weakness as being present in 33% of stroke patients [9]. In the meantime, there is a growing shortage of neurologist in practice. The situation worsens as the number of patients with neurological diseases outpaces the rate of new neurologists, the disparity will likely increase [10]. The situation is more dire in rural and underserved areas [11].

With the relatively recent development of deep learning techniques for computer vision [12], camera-based approaches enable many non-invasive applications for assistive medical diagnosis from faces analysis [13]-[15]. More specifically regarding facial weakness detection, several studies investigated classifying facial weakness from static images [16]-[22]. However, assessing facial weakness relying solely on a single static image is somewhat limited because it requires the manual and careful selection of the target image. Therefore, there is a need in the art for a simple video examination, which contains a set of image sequences and of which would therefore be more effective in identifying the signs of weakness. Therefore, there is a need in the art for automating face weak-ness assessment. For instance, three approaches depending on the type of features used may be implemented: (1) shape-based approaches; (2) appearance-based approaches; and (3) depth-based approaches.

Analyzing the anomalies in the facial geometric cues have been most popular approach to perform facial weakness detection. Researchers often detected facial landmarks and directly measured the facial geometric features, e.g., the distance and angles between landmarks, which were used to perform the classification on a single RGB image or a sequence of images [17], [18], [23]-[25]. For example, Gaber et al. [25] implemented a Kinect-based system to quantify facial paralysis by calculating a symmetry index for the eyebrows, eyes, and mouth. Guo et al. [18] computed the location and displacement of the landmarks to formulate the shape-based features for classifying the facial weakness. However, the drawback of shape-based methods is that the current facial landmark extraction algorithms are typically trained and calibrated using normal facial configuration and may suffer from poor accuracy for patients with facial weakness.

The face also exhibits specific texture and appearance information. Together with the emergence of deep learning methods, researchers have investigated the appearance-based features as an alternative. In [26], [27], the author employed the optical flow and local binary pattern on three orthogonal planes (LBP-TOP) to perform the facial weakness classification for videos. Guo et al. [20] devised a convolutional neural network (CNN) method to perform facial weakness severity classification on static image. Li et al. [28] extracted the intensity values and LBP features from various parts of the face as input features to a two-stage support vector machine (SVM) classifier to assess facial paralysis. The present inventor (e.g., Zhuang et al. [29]) developed a facial weakness classification system using the histogram of oriented gradients features. Other works also investigated the facial weakness classification using a combination of shape and appearance-based features. Haase et al. [21] and Modersohn et al. [22] located the local patches on the face and used a combination of the shape and appearance-based features from the local patches to assess the asymmetry for static images. More recently, Xu et al. proposed a Dual-path LSTM network to evaluate the facial weakness [30]. The local and global features for each frame were extracted by two autoencoder networks, then the LSTM modeled the temporal relationship and outputted the classification result. Storey et al. [31] proposed a 3D-ResNet network to classify facial weakness using the near-mouth region.

Several studies leveraged depth information to assess facial asymmetry. Bandini et al. [32] utilized a RGB-D camera to conduct the facial movement analysis for patients with amyotrophic lateral sclerosis. Alagha et al. [33] analyzed the dynamics of facial expressions in unilateral facial palsy using a sequences of 3D images. Desrosiers et al. [34] proposed to extract Dense Scalar Field features from a sets of 3D face images to evaluate the facial weakness treatment. The downsides of depth-based techniques can be hindered by the need of dedicated hardware and the fact that 3D reconstruction from depth information is often a delicate procedure that can have accuracy issues.

SUMMARY OF ASPECTS OF EMBODIMENTS OF THE PRESENT INVENTION

Facial weakness is a common sign of neurological diseases such as Bell's palsy and stroke. However, recognizing facial weakness still remains as a challenge, because it requires experience and neurological training. An aspect of an embodiment of the present invention system, method or computer readable medium provides, among other things, a framework for facial weakness detection, which models the temporal dynamics of both shape and appearance-based features of each tar-get frame through a bi-directional long short-term memory network (Bi-LSTM). An aspect of an embodiment of the present invention system, method or computer readable medium demonstrates, among other things, that: (1) the proposed algorithm achieves the accuracy, sensitivity, and specificity of 94.3%, 91.4%, and 95.7%, which outperforms other comparison methods and achieves the equal performance to paramedics; (2) the framework can provide visualizable and interpretable results that increases model transparency and interpretability; and (3) An aspect of an embodiment of the present invention system, method or computer readable medium provides, among other things, an inexpensive solution for facial weakness detection. An aspect of an embodiment of the present invention system, method or computer readable medium provides, among other things, a framework that can identify facial weakness effectively. An aspect of an embodiment of the present invention system, method or computer readable medium provides, among other things, a technology or technique that can be used by non-neurologists to more readily identify facial weakness in the field, leading to increasing coverage and earlier treatment.

An aspect of an embodiment of the present invention system, method or computer readable medium provides, among other things, e an automated and quantitative facial weakness screening framework that utilizes a Bi-LSTM network to model the temporal dynamics among the shape and appearance features. As discussed below, the experimental evaluation shows that the proposed algorithm outperforms other comparison methods, achieving the accuracy, sensitivity, and specificity of 94.3%, 91.4%, and 95.7% on a neurologists-verified facial weakness dataset. The statistical shape and texture analysis and the dynamics analysis of hidden states of Bi-LSTM network increase the interpretability and transparency of the proposed method. In addition, the same video dataset was rated by three EMS paramedics and three experienced neurology trainees (upper level hospital residents). The present inventor compares the evaluation of these human raters with the proposed method. An aspect of an embodiment of the present invention system, method or computer readable medium provides, among other things, a framework that achieves equal performance to the paramedics. Finally, an aspect of an embodiment of the present invention system, method or computer readable medium implements, among other things, a prototype on a regular laptop to demonstrate the feasibility of our study as a proof-of-concept showcase as shown in FIG. 4, where a subject 401 follows instructions presented on the screen of a camera-enabled smart device such as a laptop 403 (which may be for example, but not limited thereto, a smart phone, tablet, laptop, desktop, smart mirror, mobile device, as well as other processor based devices or machines configured for executing instructions) whose camera 405 records the examination. FIG. 4 illustrates an implementation of the algorithm of an embodiment of the present invention on a laptop 403 of a typical user scenario (FIG. 4(A)) and the graphical user interface (GUI) 407 (FIG. 4(B)). To sum up, the proof-of-concept study pertaining to an aspect of an embodiment system, method or computer readable medium sets forth that it can be beneficial to assist the paramedics to identify the facial weakness in the field or, more importantly, whenever expertise in neurology is not available either for emergency patient triage (e.g., pre-hospital stroke care) or chronic disease management (e.g., Bell's palsy rehabilitation screen), leading to increased coverage and earlier treatment. It should be appreciated that the camera may be any type of image acquisition device.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the environmental, anatomical, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value.

When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein.

The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc.

It should be appreciated that the subject may be any applicable human patient, for example.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

An aspect of an embodiment of the present invention provides, among other things, a system for analyzing facial weakness for predicting presence of one or more neurological deficits. The system may comprise: a camera; one or more memory devices configured to store instructions; and one or more processors. The one or more processor may be configured to execute the instructions to: extract the facial landmarks from a video feed received from the camera; perform landmarks and intensity normalization that removes translation, rotation, and scaling variations from the extracted facial landmarks; detect facial movement by employing an optical flow method to measure the face movement intensity and locate a target video segment where a smile configuration is evident to obtain desired a video segment; extract shape features and appearance-based features from target frames inside the desired video segment, wherein the shape features and appearance-based features are high-dimensional; project the high-dimensional shape features and appearance-based features onto a low-dimensional subspace; classify the input video using the low-dimensional representation of shape features and appearance-based features via a recurrent neural network; and in response to the classification, predict a presence of one or more neurological deficits and transmit the predication to one or more secondary source devices.

An aspect of an embodiment of the present invention provides, among other things, a computer-implemented method for analyzing facial weakness for predicting presence of one or more neurological deficits. The method may comprise: extracting the facial landmarks from a video feed received from a camera; performing landmarks and intensity normalization that removes translation, rotation, and scaling variations from the extracted facial landmarks; detecting facial movement by employing an optical flow method to measure the face movement intensity and locate a target video segment where a smile configuration is evident to obtain desired a video segment; extracting shape features and appearance-based features from target frames inside the desired video segment, wherein the shape features and appearance-based features are high-dimensional; projecting the high-dimensional shape features and appearance-based features onto a low-dimensional subspace; classifying the input video using the low-dimensional representation of shape features and appearance-based features via a recurrent neural network; and in response to the classification, predicting a presence of one or more neurological deficits, and transmitting the predication to one or more secondary source devices.

An aspect of an embodiment of the present invention provides, among other things, a non-transitory computer-readable medium storing instructions that, when executed by one or more processors, cause the one or more processors to perform operations for analyzing facial weakness for predicting presence of one or more neurological deficits. The non-transitory computer-readable medium may comprise: extracting the facial landmarks from a video feed received from a camera; performing landmarks and intensity normalization that removes translation, rotation, and scaling variations from the extracted facial landmarks; detecting facial movement by employing an optical flow method to measure the face movement intensity and locate a target video segment where a smile configuration is evident to obtain desired a video segment; extracting shape features and appearance-based features from target frames inside the desired video segment, wherein the shape features and appearance-based features are high-dimensional; projecting the high-dimensional shape features and appearance-based features onto a low-dimensional subspace; classifying the input video using the low-dimensional representation of shape features and appearance-based features via a recurrent neural network; and in response to the classification, predicting a presence of one or more neurological deficits, and transmitting the predication to one or more secondary source devices.

An aspect of an embodiment of the present invention provides, among other things, an automated and quantitative facial weakness screening framework that utilizes a Bi-LSTM network to model the temporal dynamics among the shape and appearance features. The technique is beneficial to assist the paramedics or other users to identify the facial weakness in the field or, more importantly, whenever expertise in neurology is not available either for emergency patient triage (e.g., pre-hospital stroke care) or chronic disease management (e.g., Bell's palsy rehabilitation screen), leading to increased coverage and earlier treatment. The technique provides visualizable and interpretable results to increase its transparency and interpretability. The technique provides for inexpensive solutions that can be used in areas underserved by non-neurologists to more readily identify neurological deficits such as facial weakness in the field or other environment.

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
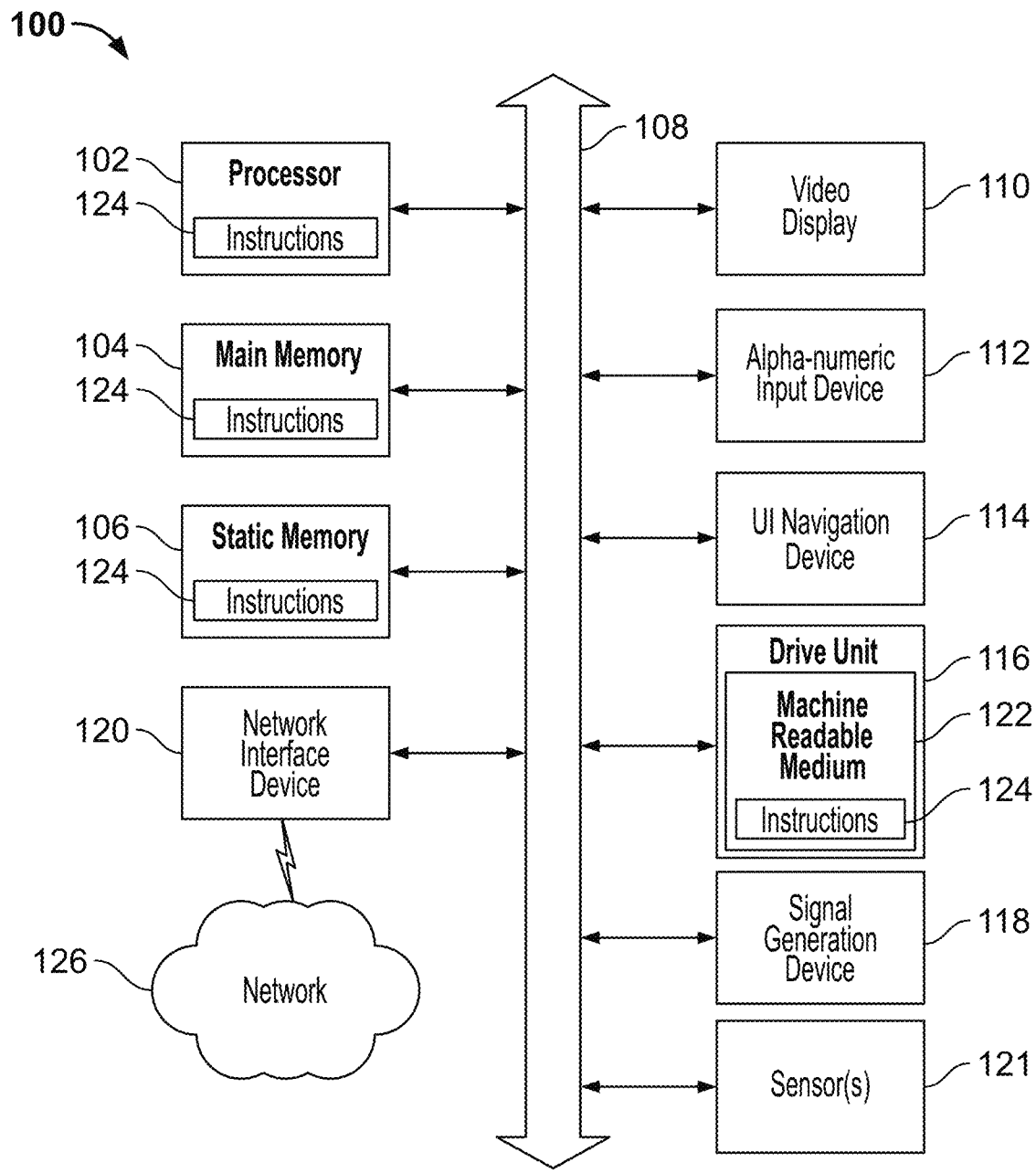
FIG. 1 is a block diagram illustrating an example of a machine upon which one or more aspects of embodiments of the present invention can be implemented.

FIG. 1 is a bock diagram of an exemplary system, consistent with disclosed embodiment. FIG. 1 represents an aspect of an embodiment of the present invention that includes, but not limited thereto, a system, method, and computer readable medium that provides for, among other things: analyzing facial weakness for predicting presence of one or more neurological deficits, which illustrates a block diagram of an example machine 100 (or machines) upon which one or more embodiments (e.g., discussed methodologies) can be implemented (e.g., run).

Examples of machine 100 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or more processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).) Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 100) and software architectures that can be deployed in example embodiments.

In an example, the machine 100 can operate as a stand-alone device or the machine 100 can be connected (e.g., networked) to other machines.

In a networked deployment, the machine 100 can operate in the capacity of either a server or a client machine in server-client network environments. In an example, machine 100 can act as a peer machine in peer-to-peer (or other distributed) network environments. The machine 100 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 100. Further, while only a single machine 100 is illustrated, the term "machine" shall also be taken to include any collection of machines that individually or jointly execute a set (or multiple sets) of instructions to perform any one or more of the methodologies discussed herein.

Example machine (e.g., computer system) 100 can include a processor 102 (e.g., a central processing unit (CPU), a graphics processing unit (GPU) or both), a main memory 104 and a static memory 106, some or all of which can communicate with each other via a bus 108. The machine 100 can further include a display unit 110, an alphanumeric input device 112 (e.g., a keyboard), and a user interface (UI) navigation device 111 (e.g., a mouse). In an example, the display unit 810, input device 417 and UI navigation device 114 can be a touch screen display. The machine 100 can additionally include a storage device (e.g., drive unit) 116, a signal generation device 418 (e.g., a speaker), a network interface device 120, and one or more sensors 121, such as a global positioning system (GPS) sensor, compass, accelerometer, or other sensor.

The storage device 116 can include a machine readable medium 122 on which is stored one or more sets of data structures or instructions 124 (e.g., software) embodying or utilized by any one or more of the methodologies or functions described herein. The instructions 124 can also reside, completely or at least partially, within the main memory 104, within static memory 106, or within the processor 102 during execution thereof by the machine 100. In an example, one or any combination of the processor 102, the main memory 104, the static memory 106, or the storage device 116 can constitute machine readable media.

While the machine readable medium 122 is illustrated as a single medium, the term "machine readable medium" can include a single medium or multiple media (e.g., a centralized or distributed database, and/or associated caches and servers) that configured to store the one or more instructions 124. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 124 can further be transmitted or received over a communications network 126 using a transmission medium via the network interface device 120 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 5:
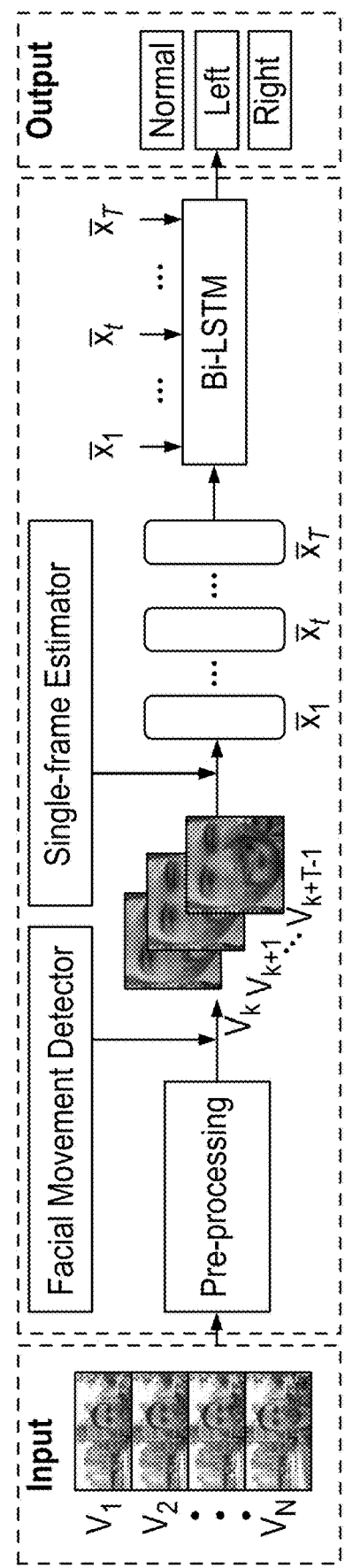
FIG. 5 schematically illustrates the architecture of an aspect of an embodiment the present invention system, method or computer readable medium.

The framework of the proposed method, system and computer readable medium is present in FIG. 5. FIG. 5 schematically illustrates the architecture of an aspect of an embodiment the present invention system, method or computer readable medium.

Given an input video sequence $\{v_t\}_{t=1}^{N}$ which a total of N frames, the frame $v_t$ is first pre-processed to remove translation, scaling, and rotation variations. The facial movement detector extracts a total of T target frames $\{v_t\}_{t=k}^{k+T-1}$ which have the maximum muscle activation and k is the index of the first target frame. Then the single frame estimator produces the shape and appearance features as $\{\bar{x}_t\}_t^T=1$ for frames $\{v_t\}_{t=k}^{k+T-1}$ where $\bar{x}_t$ is the concatenated shape and appearance based features. In an embodiment, the temporal relationship is modelled by a Bi-LSTM network, which generates the final classification output.

Still referring to FIG. 5, for a given input video, the proposed framework extracts the facial landmarks and perform landmarks and intensity normalization that removes translation, rotation, and scaling variations. Next a facial movement detector employs the optical flow approach to measure the face movement intensity and locates a video segment where a smile configuration is clearly evident, because our intent is not to use all the frames but only use the frames that have the maximum muscle activation for assessing facial weakness. Once the desired video segment is obtained, the shape and appearance-based features are extracted from the target frames inside the desired video segment. A single-frame estimator projects the high-dimensional shape and appearance-based features onto a low-dimensional subspace. Finally the framework classifies the input video using the low-dimensional representation of shape and appearance-based features via a Bi-LSTM network. The final output of the framework is left facial weakness (left), right facial weakness (right), or normal control (normal). The terminology (e.g., left, right, and normal) will be used to denote these three classes throughout the disclosure.

Figure 2:
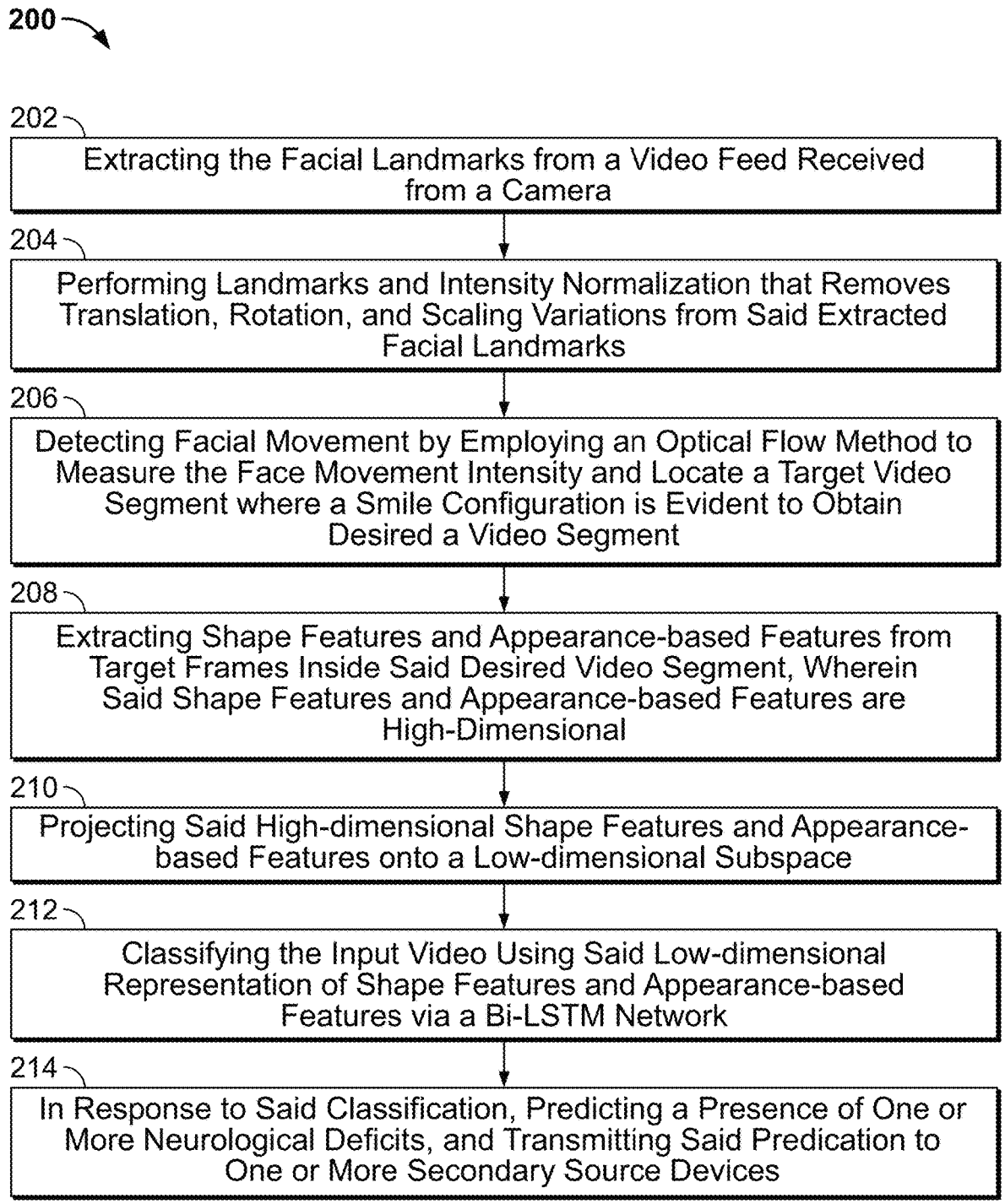
FIG. 2 is a block diagram of an exemplary process for automated detection of neurological deficits, consistent with disclosed embodiments.

FIG. 2 is a block diagram of an exemplary process for automated detection of neurological deficits, consistent with disclosed embodiments. Process 200 may be performed by processor 102 of, for example, system 100, which executes instructions 124 encoded on a computer-readable medium storage device. It is to be understood, however, that one or more steps of process 100 may be implemented by other components of system 100 (shown or not shown).

At step 202, the system 100 may extract the facial landmarks from a video feed received from said camera 405.

At step 204, the system 100 may perform landmarks and intensity normalization that removes translation, rotation, and scaling variations from said extracted facial landmarks.

At step 206, the system 100 may detect facial movement by employing an optical flow method to measure the face movement intensity and locate a target video segment where a smile configuration is evident to obtain desired a video segment.

At step 208, the system 100 may extract shape features and appearance-based features from target frames inside said desired video segment, wherein said shape features and appearance-based features are high-dimensional.

At step 210, the system 100 may project said high-dimensional shape features and appearance-based features onto a low-dimensional subspace.

At step 212, the system 100 may classify the input video using said low-dimensional representation of shape features and appearance-based features via a recurrent neural network.

At step 214, the system 100 may in response to said classification, predict a presence of one or more neurological deficits and transmit said predication to one or more secondary source devices.

Pre-Processing

Figure 6B:
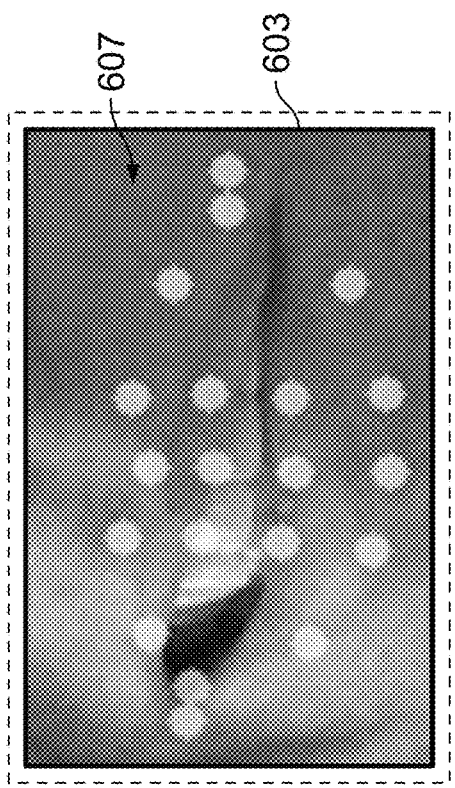
FIG. 6(B) shows the shape-based features of the near-mouth region used in this study.
Figure 6C:
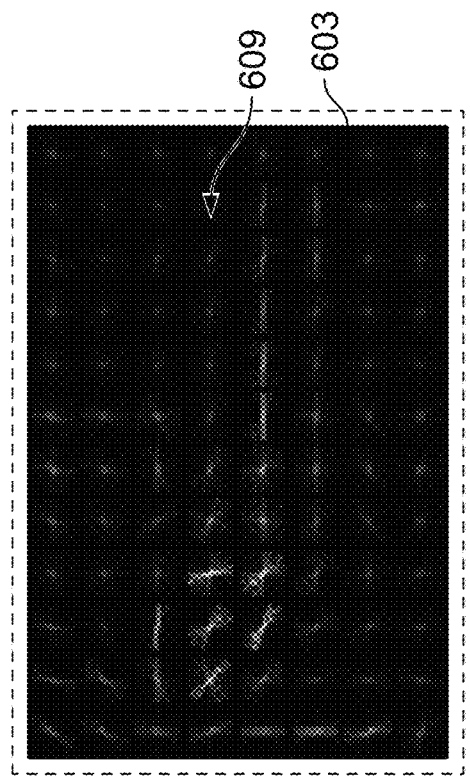
FIG. 6(C) shows the appearance-based features of the near-mouth region used in this study.
Figure 6A:
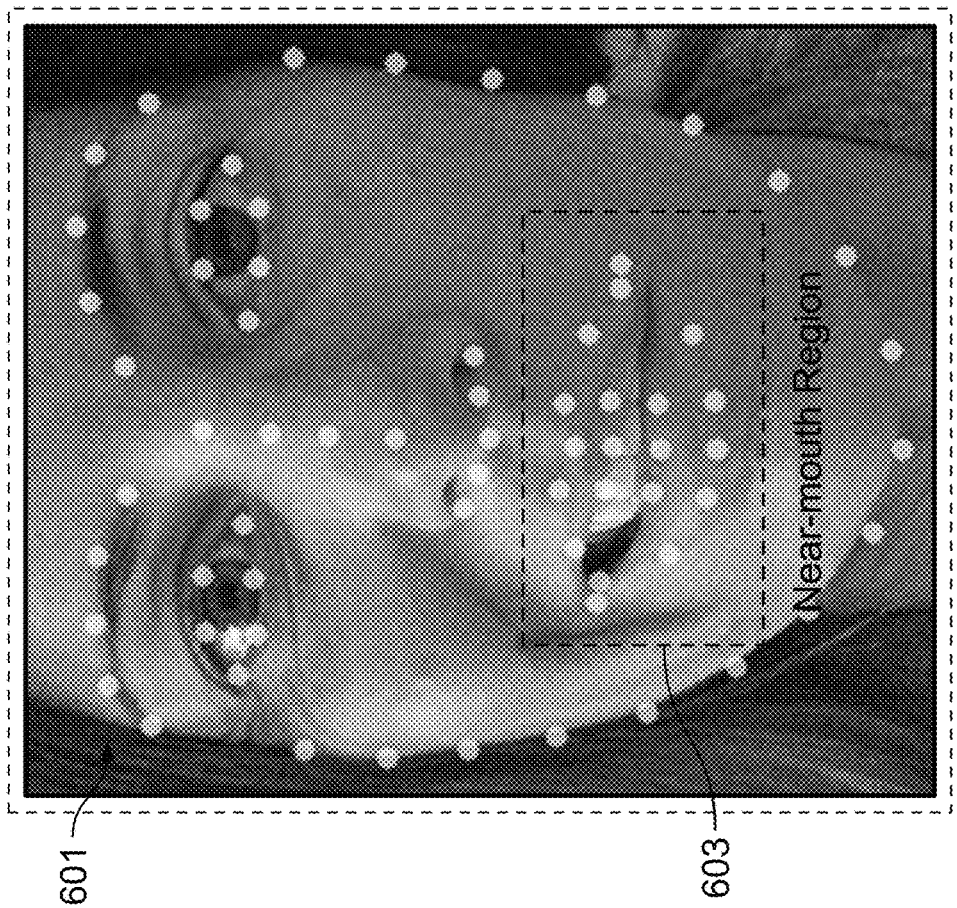
FIG. 6(A) shows an example of facial weakness with facial landmarks as demonstrated by the dots, including near mouth region.

A human face can be represented by 68 anatomically significant pairs of points, called facial landmarks. Each coordinate (x, y) specifies a facial landmark on the image. The histogram of oriented gradient (HoG) features, which compute the statistical distribution of the image gradient, are widely used for object detection [35]. An aspect of an embodiment of the present invention system, method or computer readable medium provides for, among other things, using the facial landmarks and HoG features as shape-based features and appearance-based features respectively (we will use them interchangeable throughout the disclosure). FIG. 6 shows an example of facial landmarks, shape-based features and appearances-based features for the region near the mouth. FIG. 6(A) shows an example of facial weakness 601 with facial landmarks as demonstrated by the dots, including the near mouth region 603. FIG. 6(B) shows the shape-based features 607 as demonstrated by the dots of the near-mouth region 603 used in this study. FIG. 6(C) shows the appearance-based features 609 of the near-mouth region 603 used in this study. Note that the landmarks fail to delineate the mouth shape accurately in this case. Because our data was collected from public image and video databases, the facial images contained in them are subject to random location, orientation, and size variations. An aspect of an embodiment of the present invention system, method or computer readable medium provides for, among other things, the application of a rigid body estimation method to estimate the rotation, scaling, and translation parameters that align each image in the data set to an average template [36]. After the alignment, only the region of interest (ROI) is kept. In our experiment, we evaluate the facial weakness classification scheme on two ROIs: the near-mouth region and full face.

Facial Movement Detection

Figure 7:
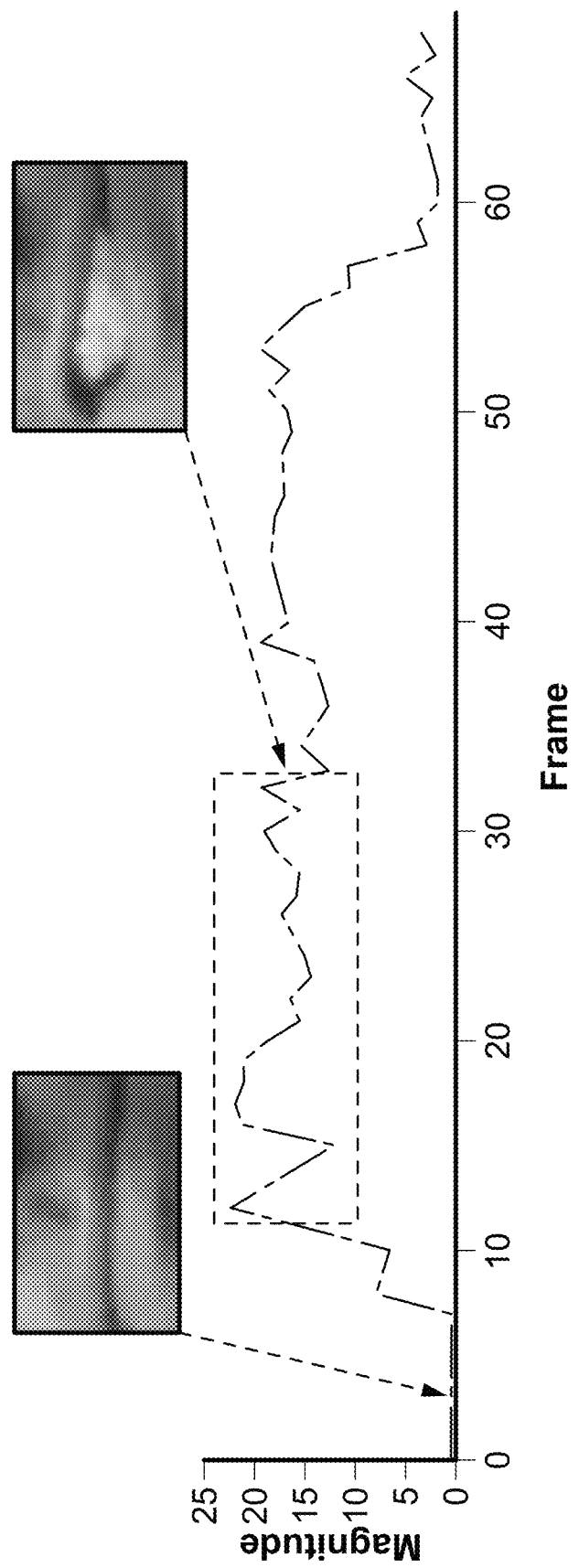
FIG. 7 graphically illustrates the facial movement detector that locates the video segment with the maximum muscle activation, as labeled in dashed-line box.

One of the goals of the facial movement detector is to locate the desired video segment that has the maximum muscle activation, as shown in FIG. 7. FIG. 7 graphically illustrates the facial movement detector that locates the video segment with the maximum muscle activation, as labeled in dashed-line box. Because the facial movement can be characterized by the displacement of pixels, an aspect of an embodiment of the present invention system, method or computer readable medium provides for, among other things, using the optical flow method to identify the full smile activation and locate the desired video segment. In an embodiment, the approach sets the first frame as the reference frame $I_0$, the optical flow estimation of the subsequent frames are computed with respected to the reference frame $I_0$ [37]. A sliding window is used to calculate the total magnitude for the T frames inside the window. Then an approach selects the window that has the largest magnitude as the target window. All T target frames inside the detected window are used for further analysis.

Single Frame Shape and Appearance Estimator

The single frame estimator aims at extracting the most discriminant shape and appearance information related to facial weakness from a single frame. In order to construct such an estimator, an aspect of an embodiment of the present invention system, method or computer readable medium provides for, among other things, modeling the pathological meaningful shape and appearance variation on an neurologist-verified image dataset that is independent of the video dataset in a supervised-learning fashion. An approach utilizes a composition of the principle component analysis (PCA) [38] and penalized linear discriminant analysis (pLDA) [39] method to perform the statistical shape and texture analysis, which is able to learn the discriminating pattern to separate between multiple classes (normal vs. left vs. right). This can be represented mathematically as $\hat{x}=W_{plda}^T W_{pca}^T x$, where x denotes either the shape feature vector or appearance feature vector. These projection matrices, $W_{pca}$ and $W_{plda}$, can be estimated using the standard PCA and pLDA techniques [38], [39]. It is worth noting that each column in the projection matrices $W_{plda}$ and $W_{pca}$ is composed of an eigenvector and defines a set of directions in the low-dimensional PCA and pLDA subspace. Using this single frame estimator not only allows us to identify the most discriminant pattern of facial weakness and provides the visualizable and interpretable result, but also facilitates the fast computation by representing high-dimensional data in a compact form. To this end, the single frame estimator generates a feature sequence by directly concatenating the estimated shape and appearance-based features for each frame in the detected target video segment $\{v_t\}_{t=k}^{k+T-1}$ as $\{\bar{x}_t\}_{t=1}^T$, where k is the index of the first target frame.

Temporal Modeling

Figure 8:
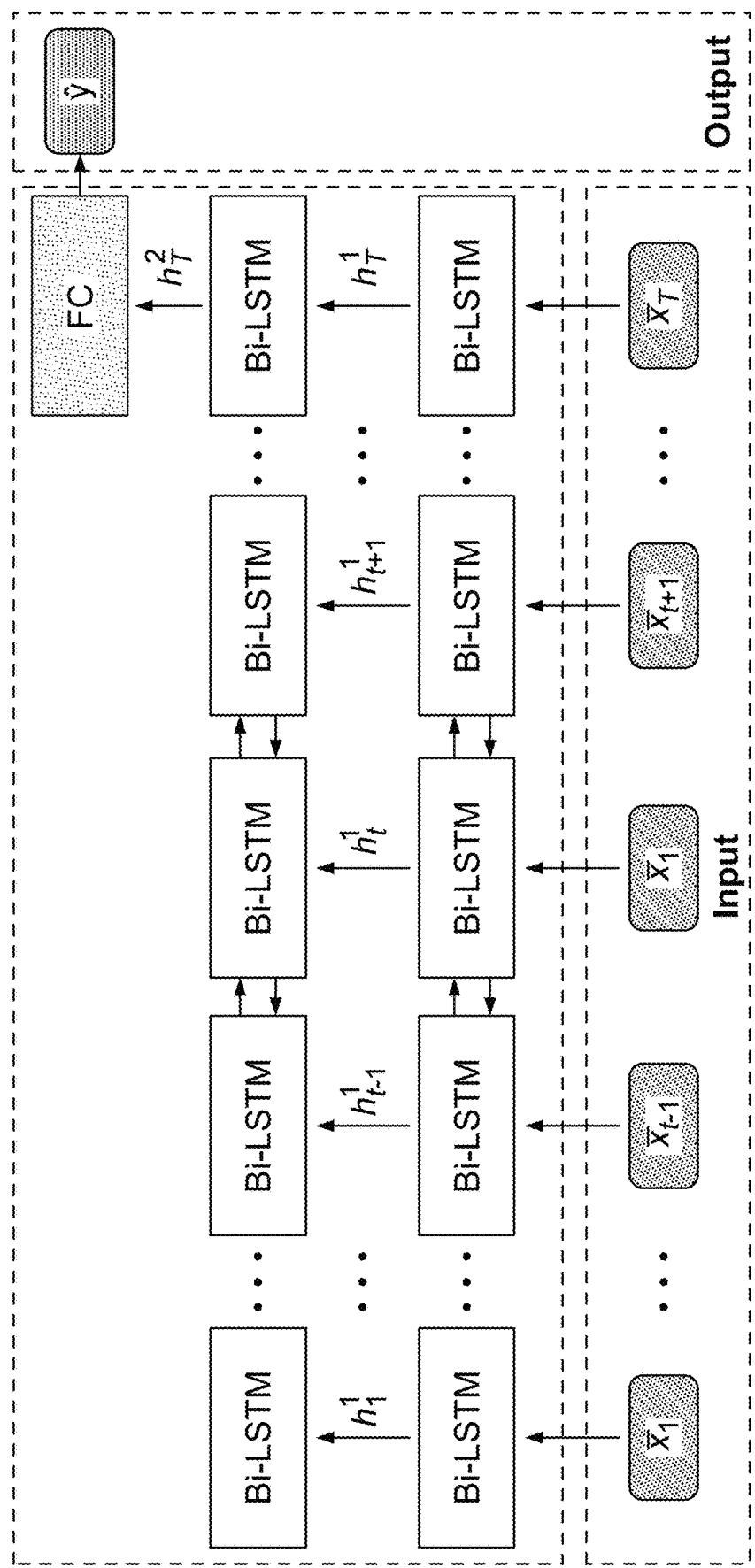
FIG. 8 schematically illustrates the network structure of the Bi-LSTM used in an aspect of an embodiment of the present invention system, method or computer readable medium.

The temporal modeling algorithm in our study seeks to predict the label j for the feature sequence $\{\bar{x}_t\}_{t=1}^T$ via a recurrent neural network (RNN) based approach. The RNN network is able to learn the temporal relationship between the image sequences and maps the learned temporal information to a sequence label [40]. An aspect of an embodiment of the present invention system, method or computer readable medium provides for, among other things, using a two-layer Bi-LSTM network to implement the RNN as shown in FIG. 8. FIG. 8 schematically illustrates the network structure of the Bi-LSTM used in an aspect of an embodiment of the present invention system, method or computer readable medium. To be precise, given the input feature sequence $\{\bar{x}_t\}_{t=1}^T$, the first Bi-LSTM layer computes the hidden state $h_t^1 = [\vec{h}_t^1, \overleftarrow{h}_t^1]$ by concatenating the forward hidden state $\vec{h}_t^1$ and backward hidden state $\overleftarrow{h}_t^1$ at time t, while the $\vec{h}_t^1$ and $\overleftarrow{h}_t^1$ can be calculated as $$\vec{h}_t^1 = f(\bar{x}_t, \vec{h}_{t-1}^1)$$
$$\overleftarrow{h}_t^1 = (\bar{x}_t, \overleftarrow{h}_{t+1}^1) \quad (1)$$

Where '.' refers to the standard LSTM update equation in a LSTM cell [40], $\bar{x}_t$ is the input at time t, $h_{t-1}^1$ and $h_{t+1}^1$ are hidden state at t−1 and t+1, and the superscript 1 of $h_t^l$ is the $l_{th}$ layer of LSTM network. Likewise, using equation (1), the $h_t^2 = [\vec{h}_t^2, \overleftarrow{h}_t^2]$ can be computed at time t. Finally, a dense layer outputs the classification result ŷ for the given input sequence as:

$$\hat{y} = W_y \cdot h_T^2 + b_y \quad (2)$$

Where $W_y$ and $b_y$ are the weight matrix and bias item of the fully-connected layer. The Experimental Setup Section below details the parameter configurations for the Bi-LSTM network.

Figure 3:
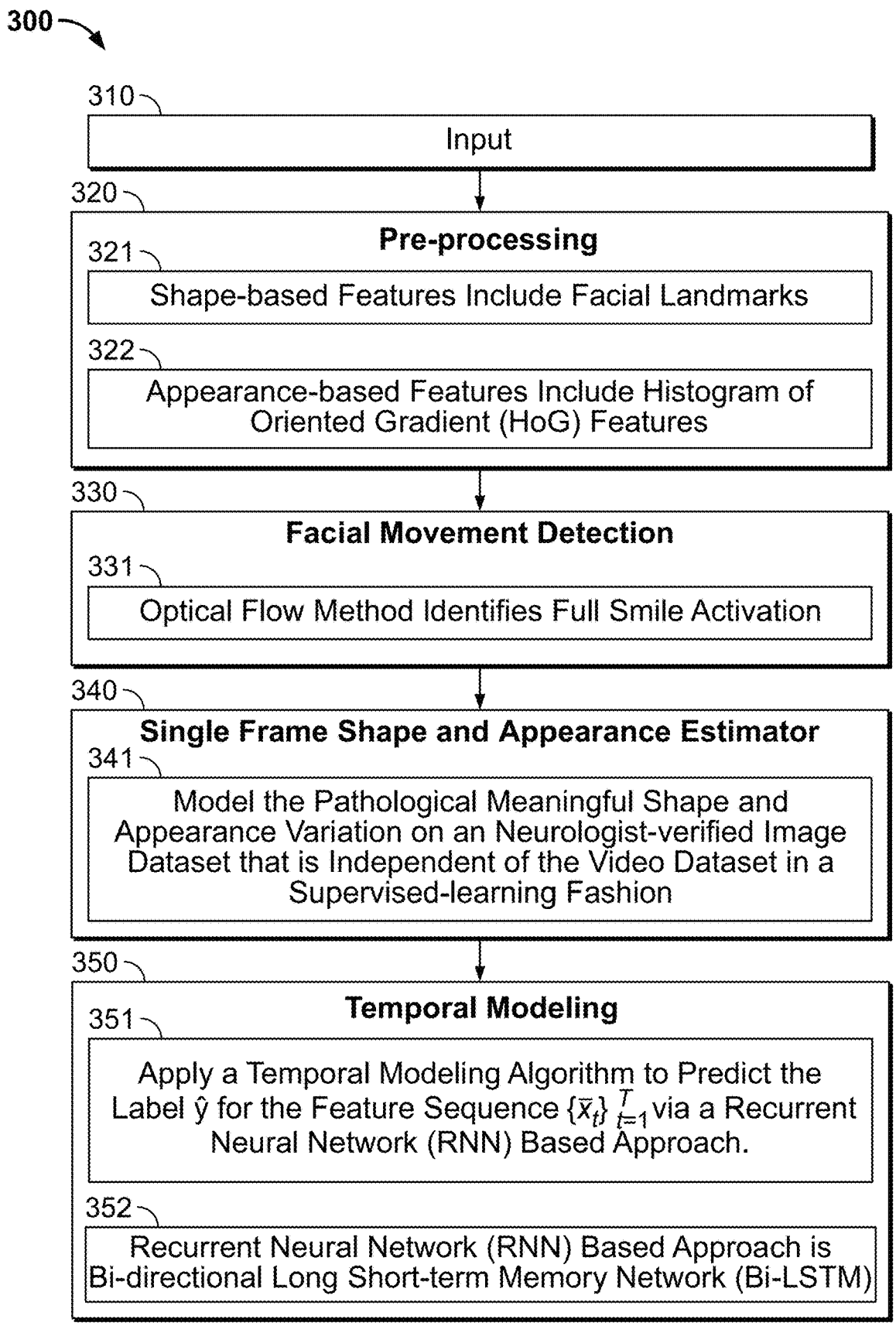
FIG. 3 is a block diagram of an exemplary algorithmic process for automated detection of neurological deficits, consistent with disclosed embodiments.

FIG. 3 is a block diagram of an exemplary algorithmic process for automated detection of neurological deficits, consistent with disclosed embodiments.

During process 300, input 310, such as images or video, may be input to pre-processing 320.

The pre-processing 320 of the process 300 may further include, 321, shape-based features include facial landmarks. The pre-processing 320 may further include, 322, appearance-based features include histogram of oriented gradient (HoG) features.

Process 300 may further include, 330, facial movement detection. The facial movement detection 330 may include, 331, optical flow method that identifies full smile activation Process 300 may further include, 340, single frame shape and appearance estimator. The single frame shape and appearance estimator 340 may include, 341, a model of the pathological meaningful shape and appearance variation on a neurologist-verified image dataset that is independent of the video dataset in a supervised-learning fashion.

Process 300 may further include, 350, temporal modeling. The temporal modeling 350 may include, 351, the application of a temporal modeling algorithm to predict the label y for the feature sequence $\{\bar{x}_t\}_{t=1}^T$ via a recurrent neural network (RNN) based approach. The temporal modeling 350 may include, 352, the recurrent neural network (RNN) based approach is bi-directional long short-term memory network (Bi-LSTM).

In summary, an aspect of an embodiment of the present invention system, method or computer readable medium provides, among other things, a framework for detecting facial weakness in videos. An aspect of an embodiment of the present invention system, method or computer readable medium outperforms other existing facial weakness detection alternatives on a neurologist-verified video dataset and achieves equal performance with paramedics. Furthermore, an aspect of an embodiment of the present invention system, method or computer readable medium provides, among other things, visualizable and interpretable results to increase its transparency and interpretability. An aspect of an embodiment of the present invention system, method or computer readable medium provides for, among other things, inexpensive solutions that can be used in areas underserved by non-neurologists to more readily identify neurological deficits such as facial weakness in the field.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

We first describe the acquisition of two independent facial weakness datasets and the corresponding verification process by three board-certified neurologists followed by the experiment setup description. The subsequent section provides the experiment results including the statistical shape and appearance analysis of the single frame estimator and performance comparisons with other approaches. Furthermore, the comparison between the proposed method and the human raters is provided. At the end of this section, a prototype of our proposed approach as a proof-of-concept is present.

Data Collection and Validation

Due to the fact that no facial weakness image and video dataset is publicly available, we assembled two independent datasets including an image dataset and a video dataset from publicly available repositories such as Google Images and YouTube. The image dataset was used to build the single-frame estimator, while the video dataset was used to evaluate the proposed video classification algorithm. It is worth noting that since neurologist diagnosis is still the gold standard for confirming the presence or absence of facial weakness, the image dataset and video dataset were verified by three board-certified neurologists using a modified NIH stroke score (NIHSS) [41]. To minimize the possibility that three clinical raters made the same mistake, the median score of their ratings serves as the ground truth.

The image dataset acquisition and verification is described in [19]. In total, the image dataset consists of 236 images, including 88 normal control images, 76 left facial weakness images, and 72 right facial weakness images. Then it is augmented by flipping the images horizontally. The video dataset was collected by three senior medical students. The data acquisition protocol included the videos containing exactly one subject who faces the camera directly with full face in view and has a neutral expression at the beginning and shows a prominent smile thereafter to ensure the presence of maximum muscle activation. Three board-certified neurologists independently reviewed the videos. To classify presence or absence of face deficits, the 5-point scale NIHSS scores were converted into a modified 3-point scale: 1 denotes pathology absent, 2 denotes pathology indeterminate, and 3 denotes pathology present. Then we computed a median score from the three neurologists to serve as the ground truth. The videos with a median score of one or three were selected in our study, resulting in 43 left facial weakness videos, 50 right facial weakness videos, and 96 normal videos (72 men vs. 117 women and 155 light-skinned vs. 34 dark-skinned in terms of demographics information).

Experimental Setup

This section specifies or sets forth the experimental setup. We set the window length T, which equates to the length of the subject having maximum muscle activation, as 0.83 seconds (20 frames in our case). A detailed discussion on the selection of parameter T is available in the Example and Experimental Results Set No. 2 Section below. The ensemble of regression trees (ERT) algorithm [42] was chosen to perform facial landmark extraction owing to its high performance [43]. Two ROIs were analyzed in our study: near-mouth region and the full face. After the normalization, near-mouth region was resized as 128 by 200 pixels and the full face was resized as 256 by 256 pixels. The parameter configuration for the HoG features was: the number of orientation bins in each cell was 12 and a cell consists of 16 by 16 pixels. In terms of parameter setup for the PCA method, the components that can cover 98% of the variance of HoG features were kept and the components that can cover 96% of the variance of landmark features were kept. For the pLDA method, the $\alpha$ for HoG features was set to 10 and for landmark features was set to 0.1 according to [39]. The Bi-LSTM network consisted of two Bi-LSTM layers, each Bi-LSTM layer had 64 hidden units. We utilized the Adam optimizer to optimize the network. The learning rate for Adam optimizer was set to 0.001. The $\beta_1$ and $\beta_2$ were set to 0.9 and 0.999, respectively. We report the accuracy averaged over these 5 times using stratified 5-fold cross-validation scheme. To evaluate the performance of the proposed algorithm, we compared it with the LBPTOP based approach [26], 3DResNet (or 3DPalsyNet) [31], Dual-path LSTM [30], 2DCNN+RNN [44], and Two-stream LSTM [45]. The implementation details of these comparison methods are provided in the supplemental material [55].

Results

Figure 9:
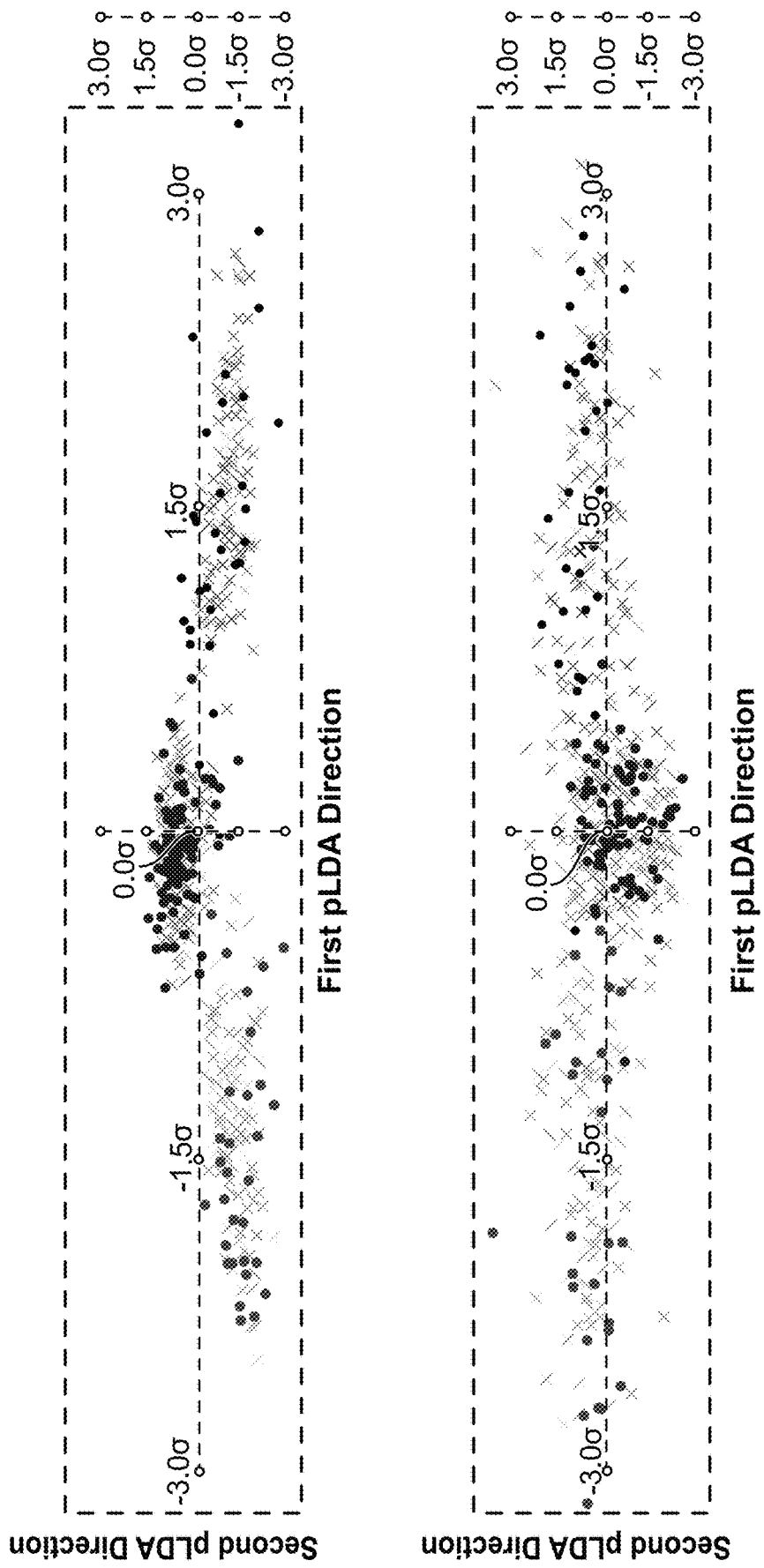
FIG. 9 graphically depicts the distribution of projection of appearance-based features (top graph) and shape-based features (bottom graph) onto the pLDA subspace for image dataset: normal (blue), right (black), and left (red).
Figure 10:
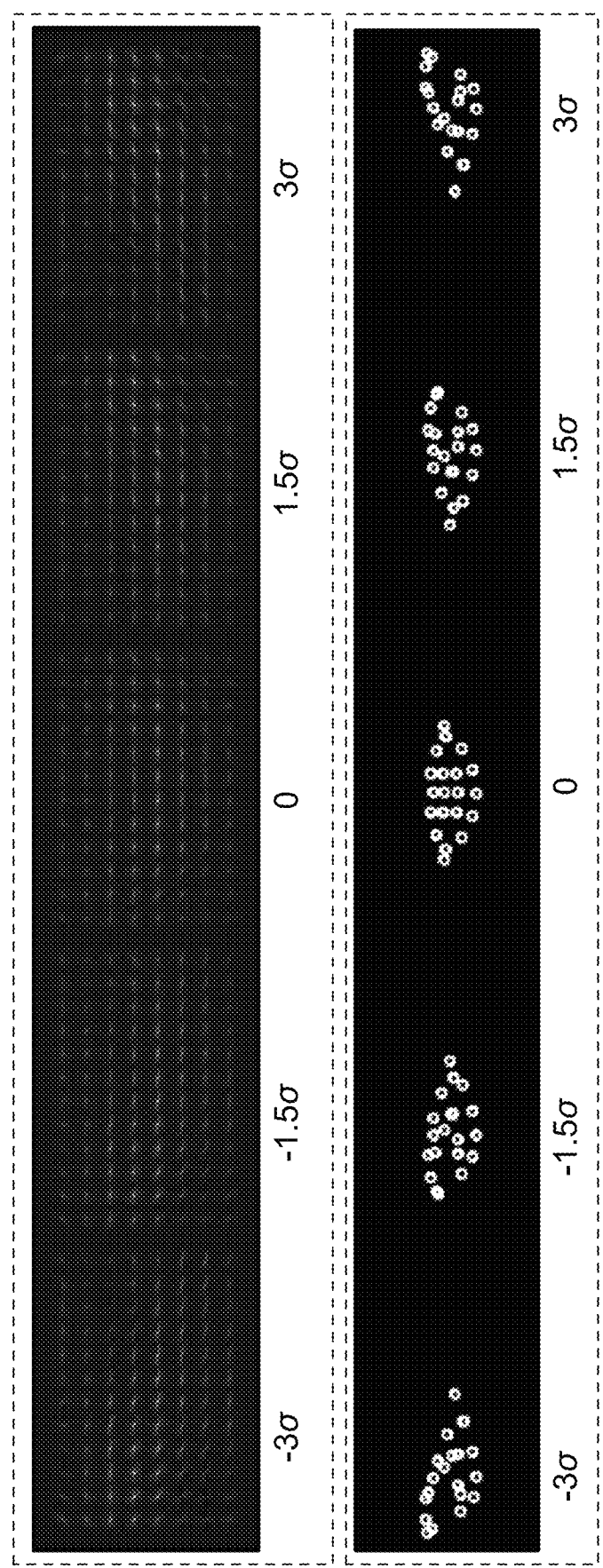
FIG. 10 graphically depicts modes of variation along first pLDA direction in HoG features space (top graph) and in landmark features space (bottom graph).

1) Shape and Appearance Analysis for Static Frames: Here we show that the single frame estimator can capture the pathological facial weakness. FIG. 9 shows the results of projecting the shape and appearance-based features of training (in lighter color) and testing samples (in darker color) onto a smaller pLDA subspace. FIG. 9 graphically depicts the distribution of projection of appearance-based features (top graph) and shape-based features (bottom graph) onto the pLDA subspace for image dataset: normal (blue), right (black), and left (red). The cross symbols with lighter color are training samples while the round symbols with darker color are testing samples. The x-axis is the first pLDA direction and y-axis is the second pLDA direction. One observation is that the between-class discriminatory information still maintains, while the dimension of HoG features and landmarks features is significantly reduced. To quantitatively assess the discriminatory information of the shape based features and appearance based features, we perform a statistical test (McNemar's test [46], [47]) and show that the classification performance difference between the shape-based features and appearance-based features is statistically significant (p-value <0.001) using a 5-fold cross validation scheme. To further show that meaningful pathological features can be captured by the proposed single-frame estimator, we visualize 5 modes of variation for appearance and shape based features along the most discriminant pLDA direction for the near mouth region. FIG. 10 is produced by computing the value of $\mu+a\alpha\sigma$ and projecting it back to the original feature space, where is the mean features, $\alpha$ is the features variation along first pLDA direction, and a is the coefficient that specifies the degree of variation. FIG. 10 graphically depicts modes of variation along first pLDA direction in HoG features space (top graph) and in landmark features space (bottom graph). A larger value of a indicates a higher degree of shape and appearance deformation from the normal shape and appearance features (central column). It is worth noting that the sign of $\alpha$ contains the class-related information (normal, left, and right) while the amplitude of $\alpha$ implies the degree of deformation. Together, FIGS. 9 and 10 show that the single-frame estimator is able to classify and capture the clinically meaningful facial asymmetry using both shape and appearance-based features. Another benefit of our analysis is that projecting the high-dimensional features onto a low-dimensional subspace reduces the computation complexity and increases the computation efficiency.

Figure 11A:
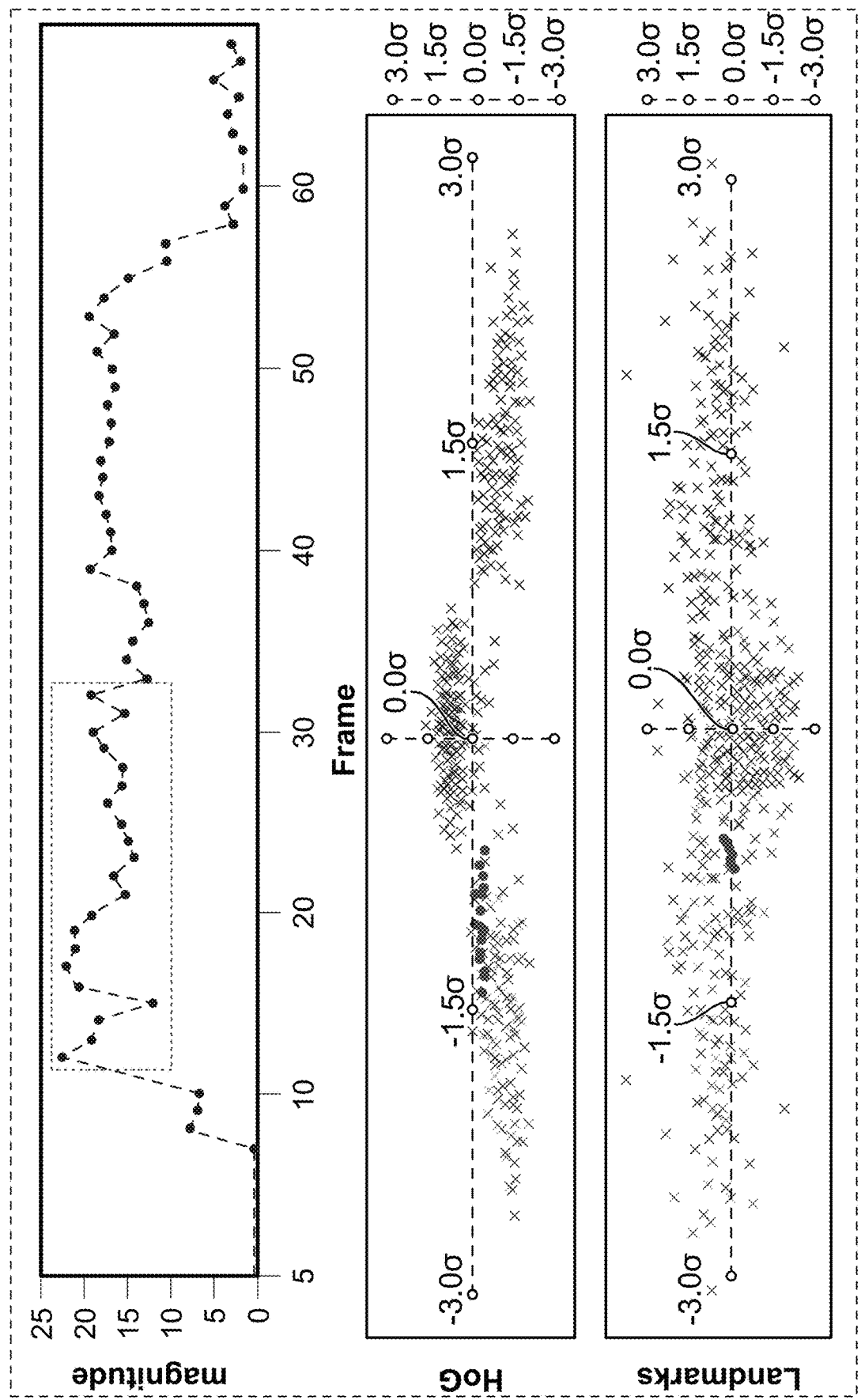
FIG. 11(A) graphically demonstrates an example of video classification, namely left facial weakness, in detail.
Figure 11B:
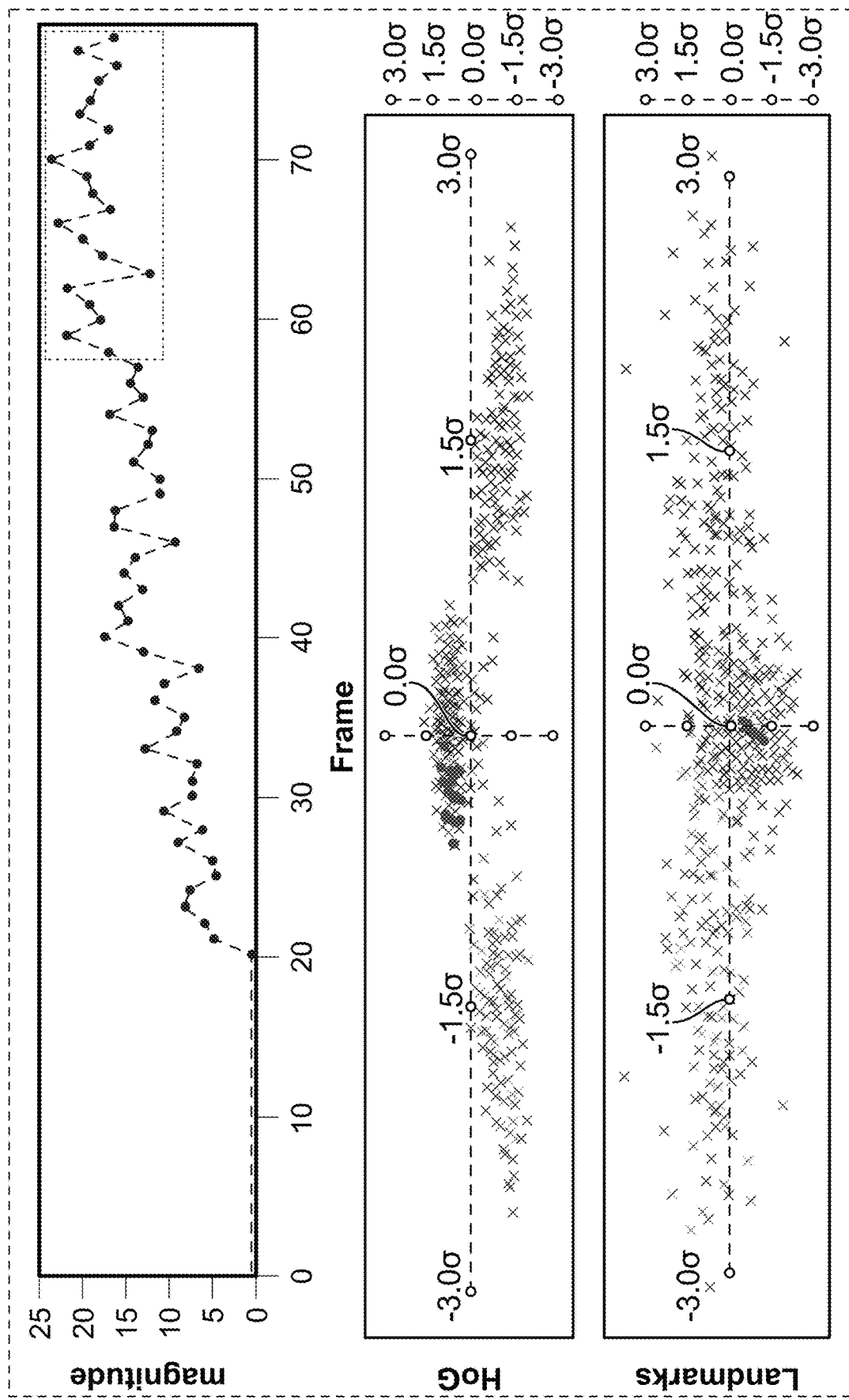
FIG. 11(B) graphically demonstrates an example of video classification, namely normal, in detail.

2) Video Classification Results: FIG. 11(A) and FIG. 11(B) illustrates two concrete examples to illustrate how the proposed approach works. FIG. 11 graphically demonstrates two examples of video classification, namely left facial weakness (FIG. 11(A)) vs. normal (FIG. 11(B)) in details. In each subfigure, the first row shows the optical flow measurement where the video segment that has the largest muscle activation is identified and highlighted using the red dashed-line box. Two rows at the bottom show the low-dimensional representation of HoG features and landmarks features (plotted in green dots) for each target frame inside the video segment. First, the framework measures muscle activation and detects a relevant video segment as highlighted in the red dash-lined window. Then, the single-frame estimator projects the shape and appearance-based features of each target frame inside this video segment onto the two-dimensional pLDA subspace as shown in the middle and bottom row. Each green dot represents a target frame inside the video segment. This shows that the learned optimal representation of facial weakness from the image dataset by the single-frame estimator is not overfitting and is effective for the video dataset. Table II presents the evaluation results of the proposed method for two different ROIs (near-mouth vs. full face). The proposed method achieves the accuracy of 88.3%, sensitivity of 82.5%, and specificity of 91.2% for the full face region, and accuracy of 94.3%, sensitivity of 91.4%, and specificity of 95.7% for near-mouth region. However, we also note that there are several misclassified cases due to the lighting and appearance variations, which degrade the image quality and appearance variations, which degrade the image quality and cause inaccurate ROI segmentation. The proposed method shows that the near-mouth region contains more discriminant information to identify facial weakness than that of full face, which is also verified by other studies [18], [26].

Table III presents the comparison results with other existing facial weakness detection alternatives. First, we note that the proposed algorithm outperforms other methods in terms of ac-curacy, sensitivity and specificity. To quantitatively assess the performance difference between the proposed algorithm and other comparison methods, a statistical test (Cochran's Q test, which is a generalized method of McNemar's test used for evaluating multiple classifiers [46], [47]) is conducted to show that the performance difference of our method with other methods shown in Table III is statistically significant (p-value <0.001). Secondly, the performance varies significantly among the other deep learning based methods. The 3DResNet achieves the best performance.

When comparing with the shallow 3DCNN, a deep learning baseline method for comparison, the higher performance of 3DResNet demonstrates that both of the depth of the network and the architecture of the network affect classification accuracy. In terms of RNN-based methods' performance, the results demonstrate that LSTM network architecture is effective to learn the temporal discriminate information to classify facial weakness. The Dual-path LSTM and two-stream LSTM obtain a better performance compared with the CNN+LSTM approach, this is because the Dual-path LSTM takes local information from the image patches into account and the two-stream LSTM incorporates motion information from the optical flow features. Both operation increase classification performance [48].

Figure 12:
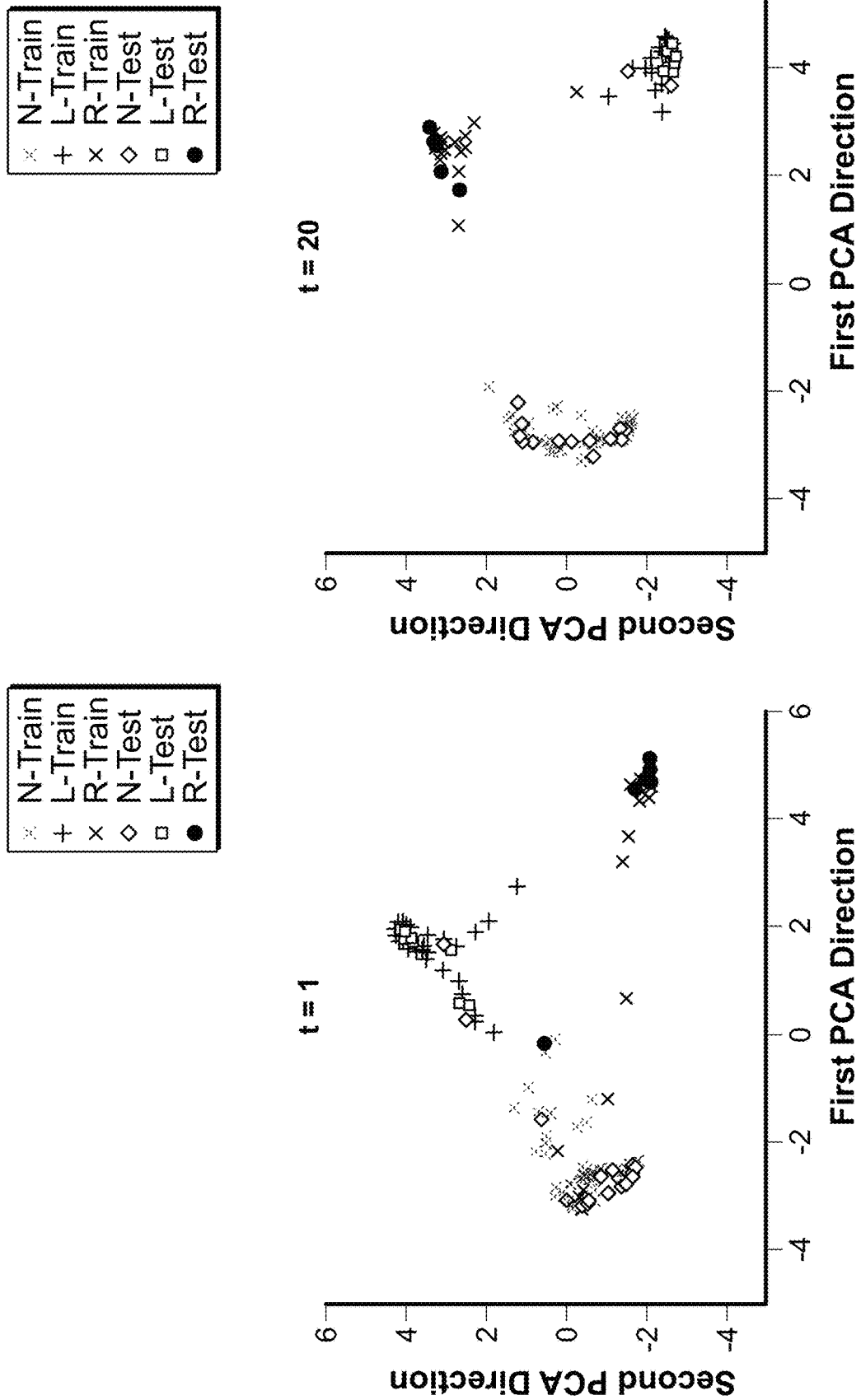
FIG. 12 graphically illustrates the evolution of hidden state of BiLSTM at time t=1 and t=20, respectively.

To further increase the interpretability and transparency of the proposed method, we examine the geometric structure of Bi-LSTM hidden states $h_t^2$ at time t, by projecting it onto a 2-dimensional PCA subspace [49]. To be precise, we perform $h_{t=1}^2$ for all the training samples. Then the projection of the hidden states $h_{t=1}^2$ for all training samples and testing samples onto the top two principle components is shown in left panel of FIG. 12. The right side of FIG. 12 shows the projection of Bi-LSTM hidden states $h_{t=20}^2$ at time T (last frame) using the same PCA setup. Overall, FIG. 12 illustrates that the hidden states of Bi-LSTM evolve alone in a low-dimensional subspace and become more separable when Bi-LSTM continues to take the input. FIG. 12 graphically illustrates the evolution of hidden state of BiLSTM at time t=1 and t=20, respectively. Three symbols represent different respective classes. The class for "normal" is represented by the following symbols: ✗ and ◇. The class for "left" is represented by the following symbols: ✚ and ☐. The class for "right" represented by the following symbols: ✗ and ●. The sample with symbols ✗, ✚ and ✗ represents the training cases while the sample with symbols ◇, ☐, ● and represents the testing cases. The X-axis is the first PCA direction and Y-axis is the second PCA direction.

TABLE II

PERFORMANCE OF PROPOSED METHOD

| | Acc. | Sens. | Spec. |
|---|---|---|---|
| Face | 88.3 ± 1.8% | 82.5 ± 2.7% | 91.2 ± 1.3% |
| Near-mouth | 94.3 ± 2.1% | 91.4 ± 3.2% | 95.7 ± 1.6% |

TABLE III

COMPARISON RESULTS

| | Acc. | Sens. | Spec. |
|---|---|---|---|
| LBP-TOP [26] | 84.9 ± 7.8% | 77.3 ± 11.8% | 88.7 ± 5.9% |
| Shallow 3DCNN | 69.3 ± 1.9% | 54.0 ± 2.9% | 76.9 ± 1.4% |

TABLE III-continued

COMPARISON RESULTS

|  | Acc. | Sens. | Spec. |
|---|---|---|---|
| Dual-path LSTM [30] | 77.1 ± 5.8% | 65.6 ± 8.7% | 82.8 ± 4.3% |
| 3DResNet [31] | 82.0 ± 4.8% | 73.0 ± 7.2% | 86.5 ± 3.6% |
| CNN + LSTM [44] | 71.4 ± 5.1% | 57.1 ± 7.7% | 78.58 ± 3.8% |
| Two-stream LSTM [45] | 80.5 ± 9.9% | 70.7 ± 14.9% | 85.3 ± 7.48% |
| Bi-LSTM (ours) | 94.3 ± 2.1% | 91.4 ± 3.2% | 95.7 ± 1.6% |

TABLE IV

PERFORMANCE COMPARISON WITH HUMAN RATERS

|  | Bi-LSTM | Paramedics | Residents |
|---|---|---|---|
| Accuracy | 94.3% [90.2%-98.4%] | 92.6% [90.1%-94.7%] | 97.9% [96.4%-99.1%] |
| Sensitivity | 91.4% [85.1%-97.7%] | 87.8% [83.9%-91.7%] | 96.4% [93.9%-98.5%] |
| Specificity | 95.7% [92.6%-98.8%] | 99.3% [98.2%-100.0%] | 99.7% [98.9%-100.0%] |

3) Comparison with Clinical Raters: In order to compare the performance of our algorithm with human raters, three EMS paramedics and three upper level residents rated our video dataset using the same protocol described above. The relative experience of the three paramedics included an Emergency Medical Technicians (EMT) with seven years of experience total and five years of experience as an advanced life support provider, a nationally registered paramedic with over 10 years of experience, and an entry level EMT with one year of experience. The three neurology residents have three years of highly-focused and systematic neurology training. Table IV shows the accuracy, sensitivity, and specificity with 95% confidence interval for the proposed framework, paramedics, and senior neurology trainees respectively. The results demonstrate that the senior neurology trainees achieve the highest performance for all three evaluation metrics. Our algorithm performance is reaching the level of residents and equivalent to the paramedics. The paramedics have the higher specificity as compared to the specificity of the proposed framework, while the proposed algorithm has better sensitivity. We also perform statistical tests for the comparison between the proposed algorithm and human raters using the McNemar's test [46], [47]. The statistical tests show that there is no significant difference between the performance of our algorithm and the paramedics performance' (p-value=0.091) while there is a significant difference between our algorithm and the residents (p-value <0.001). Furthermore, in order to quantify the disagreement among the human rates, we compute the Fleiss Kappa scores (a measure of agreement among individuals within a group) for the paramedics and resident. The paramedics achieved a Fleiss Kappa statistic of 0.806 (95% CI [0.724, 0.888], p-value <0.001), while the residents had greater agreement at 0.921 (95% CI [0.866, 0.976], p-value <0.001). The disagreement among paramedics is larger possibly because of lack of extensive neurological training. The high Kappa score of the residents indicates that the rating among residents are more consistent and reliable. This may be related to the fact that the certified neurologists also trained the neurology trainees.

4) Prototype Development: We developed a prototype that integrated the proposed algorithm and a GUI to allow users to interact with the framework in real-time. The prototype is running on a regular laptop PC with an Intel Dual-Core i7 processor, 16 GB of RAM, 512 GB of space, and an integrated graphics card. The webcam is a Logitech C920 HD PRO webcam [50]. The software is coded in Python 3.5 with the standard libraries such as PyQt for GUI interface design. The prototype implementation is further elaborated in the Example and Experimental Results Set No. 2 Section below.

Discussion

In this pilot study, we investigated a novel method to classify facial weakness on videos and evaluated it on a neurologists-verified dataset. In the evaluation, we comprehensively evaluated the proposed method with the other comparison methods as well as the clinical raters on a neurologist-verified dataset. The proposed method outperformed the comparable methods. In addition, as an indispensable aspect of the biomedical application, the interpretability become increasingly significant for recent biomedial applications [51], in order to address this issue, the proposed work provided visualizable and interpretable results to increase the model transparency, by showing that the proposed framework is able to capture variations of landmark and appearance-based features that are associated with facial weakness. Furthermore, we also tentatively showed that how the Bi-LSTM network models the temporal evolution of latent state with respect to the inputs. Another important implication of our study is that the proposed method achieved equal performance with the paramedics on our neurologists-verified dataset, which opens a new opportunity of providing clinical assistance to non-neurologists (e.g., paramedics) to increase the coverage of neurological prehospital care.

From this pilot study, we gain a substantial amount of experiences and lessons. First, our experience show that building such an online facial weakness dataset is not only time-consuming and labor intensive but also expensive, because a large amount of time is required for research coordinators to collect and curate the videos based on the data acquisition protocol. The verification process to confirm the presence of facial weakness performed by the clinician investigators, as well as the ratings from the hospital residents and EMS paramedics, is more costly owing to the expensive medical expertise when compared with other computer vision crowdsourcing task [52]. It is worth noting that collecting a real-patient dataset will be much challenging due to the prevalence of the disease, heterogeneity of symptom manifestations, and patient privacy standards. However, our experience gained from assembling this online dataset will lay a solid foundation for us to enroll the real patient and avoid potential pitfalls. We note that the study has several limitations. First, due to the fact that the video dataset is created from open access repositories and lack of the corresponding in-person examinations and medical information of the same person, all three board-certified neurology experts had the same possibility to make the same mistakes for ground truth labeling. To minimize this issue, we asked the experts to evaluate the dataset independently and only the data with the concordant ratings was used in our study. Secondly, we also notice that head pose issue is significant issue for face analysis which can lead to landmark detection failure and analysis error, as stated in [53]. To address this issue, in the experiments, we designed the data collection protocol to exclude several videos where the subject does not face the camera directly with a full view. In the prototype implementation, a head pose estimation algorithm is integrated to check the subject's head pose and give the corrective instructions throughout the examination. It is worth noting that multiple videos experienced facial landmark detection failures due to the lighting and appearance variations. This because locating facial landmarks on "in-the-wild" videos is still a challenging task and active research area [43]. In order to address aforementioned issues, the future effort are required to bridge the proof-of-concept to clinical transition gap. To be specific, our future work will include creating a facial weakness video database from real patients with clinical diagnosis, imaging findings, and electronic health records. Then, we will test the proposed framework on the real patient dataset to improve the generalizability of the proposed method. Our effort will also seek to train a dedicated facial landmark extractor by leveraging our image and video dataset to improve the landmark extraction accuracy.

Conclusion

We proposed a framework for detecting facial weakness in videos. We experimentally demonstrated that the proposed method outperforms other existing facial weakness detection alternatives on a neurologist-verified video dataset and achieves equal performance with paramedics. Furthermore, the proposed method provides visualizable and interpretable results to increase its transparency and interpretability. The prototype shows promise for inexpensive solutions that can be used in areas underserved by non-neurologists to more readily identify neurological deficits such as facial weakness in the field.

Example and Experimental Results Set No. 2
(Supplemental Material)

Comparison Methods Implementation

In order to compare with our algorithm, we implemented two types of comparison methods for a comprehensive evaluation. The first type of methods are developed for facial weakness detection, including a traditional machine learning based method (LBP-TOP [26]) and two deep learning alternatives (3DResNet [31] and Dual-path LSTM [30]) Furthermore, we also compare our algorithm with other mainstream deep learning video classification methods (CNN+LSTM [44] and two-stream LSTM [45]). To be specific, we use the following parameters to configure the LBPTOP approach: the radius along X axis, Y axis, and T axis are 1, 1, and 2 respectively, and the number of neighbor points are 8 for the XY plane, XT plane, and YT plane. The 3DResNet and Dual-path LSTM are implemented as discussed in [30], [31]. The shallow three-dimensional convolutional neural networks (3DCNN) serves as the performance baseline for deep learning based method, which consists of two convolutional layers. The number of filters and kernel size of first convolutional layer are 32 and 5×5×5, while the second layer are 48 and 3×3×3 respectively. A batch normalization (BN) layer is used after each convolutional layer. Then a ReLu layer, a dropout layer with drop rate of 0.2, and a maxpooling layer with kernel size of 2 generate the feature maps. Finally, a composition of two affine layers makes the classification. Another popular deep learning based video classification alternative makes use of a combination of CNN and RNN. To be specific, the CNN network learns the optimal representation of each individual frame while the RNN network models the changes of these spatial features along the temporal axis. We also implement a CNN+RNN (or CNN+LSTM) network based on [44]. The CNN has 4 convolutional layers with kernel numbers of 64, 128, 256, and 512, whose kernel size are 5×5, 3×3, 3×3, and 3×3 respectively. Then each convolutional layer is followed by a BN layer and a ReLu layer. Then a dropout layer with dropout ratio of 0.5 is applied. A global maxpooling layer with kernel size of 2 reduces the dimension of feature map from the CNN. A composition of two fully connected layer with 1024 nodes generates the feature map for each individual frame. Then the RNN network is implemented as a two-layer LSTM, each layer has 1024 hidden units. A fully connected layer with 512 nodes is applied on the final output of the LSTM network to produce the classification result. More recently, multiple studies indicate that incorporating the motion information, e.g, the optical flow [45], [48], [54], increases the video classification performance. We adopt this two-stream LSTM architecture as discussed in [45] for our study. To be precise, the two-stream LSTM utilizes one spatial CNN network to extract the spatial information from each frame and another motion CNN network to extract the motion information from the stacked optical flow, respectively. Then a LSTM network concatenates the outputs from these two CNN networks and learns the long-term dependency. In our implementation of the two-stream LSTM, its spatial CNN network shares the similar configuration with CNN+RNN method as discussed above. The motion CNN network has three convolutional layers. For each convolutional layer, a BN layer and a ReLu layer are applied thereafter. The kernel sizes for each convolutional layer are 5×5, 3×3, and 3×3. The number of convolutional kernel is 64, 128, and 256. After the ReLu layer, a maxpooling layer with kernel size of 2 is used. Then an affine layer with 1024 nodes produces the feature map. Finally, the feature maps from motion CNN network and spatial CNN network are concatenated and input to a two-layer LSTM with 1024 hidden units, which generates the classification prediction result.

Window Length T Selection

Figures 4A, 4B:
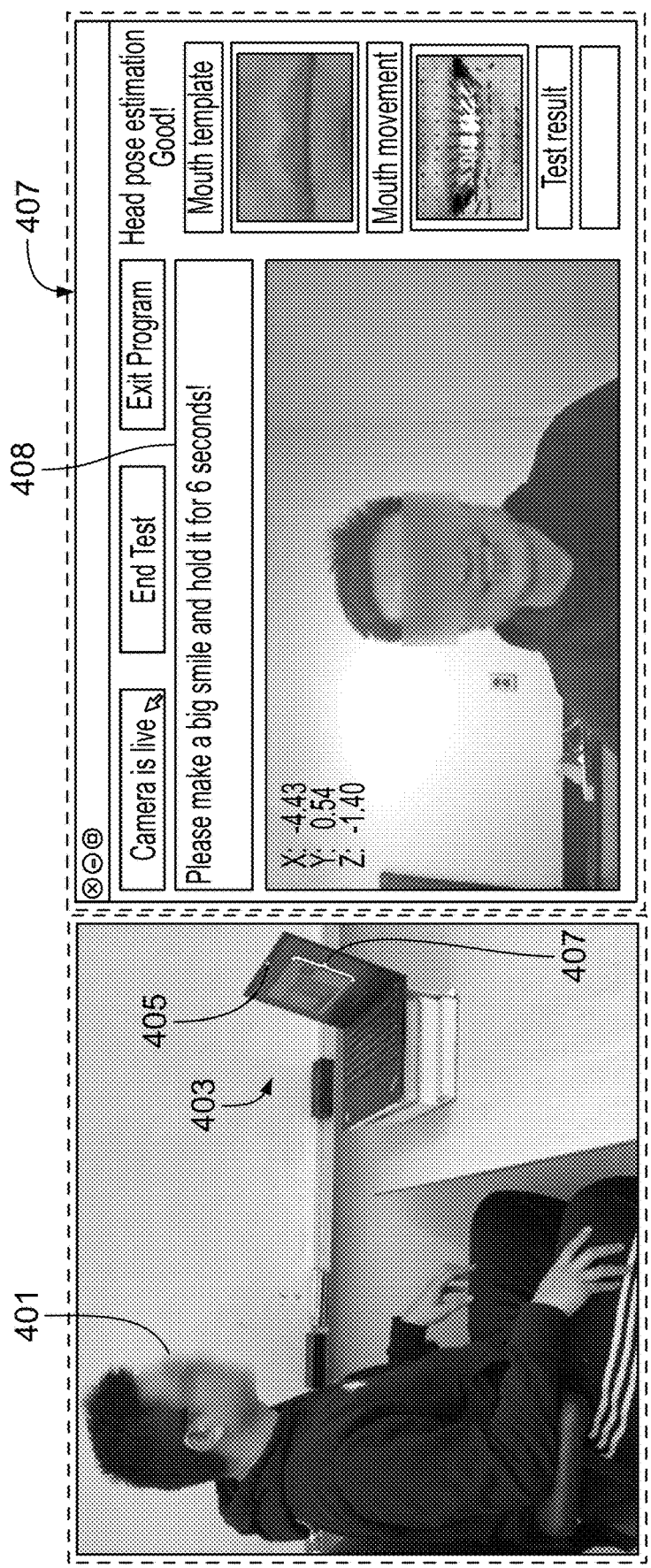
FIG. 4(A) illustrates an implementation of the algorithm of an embodiment of the present invention on a laptop of a typical user scenario.
FIG. 4(B) illustrates an implementation of the algorithm of an embodiment of the present invention on the graphical user interface (GUI).
Figure 13:
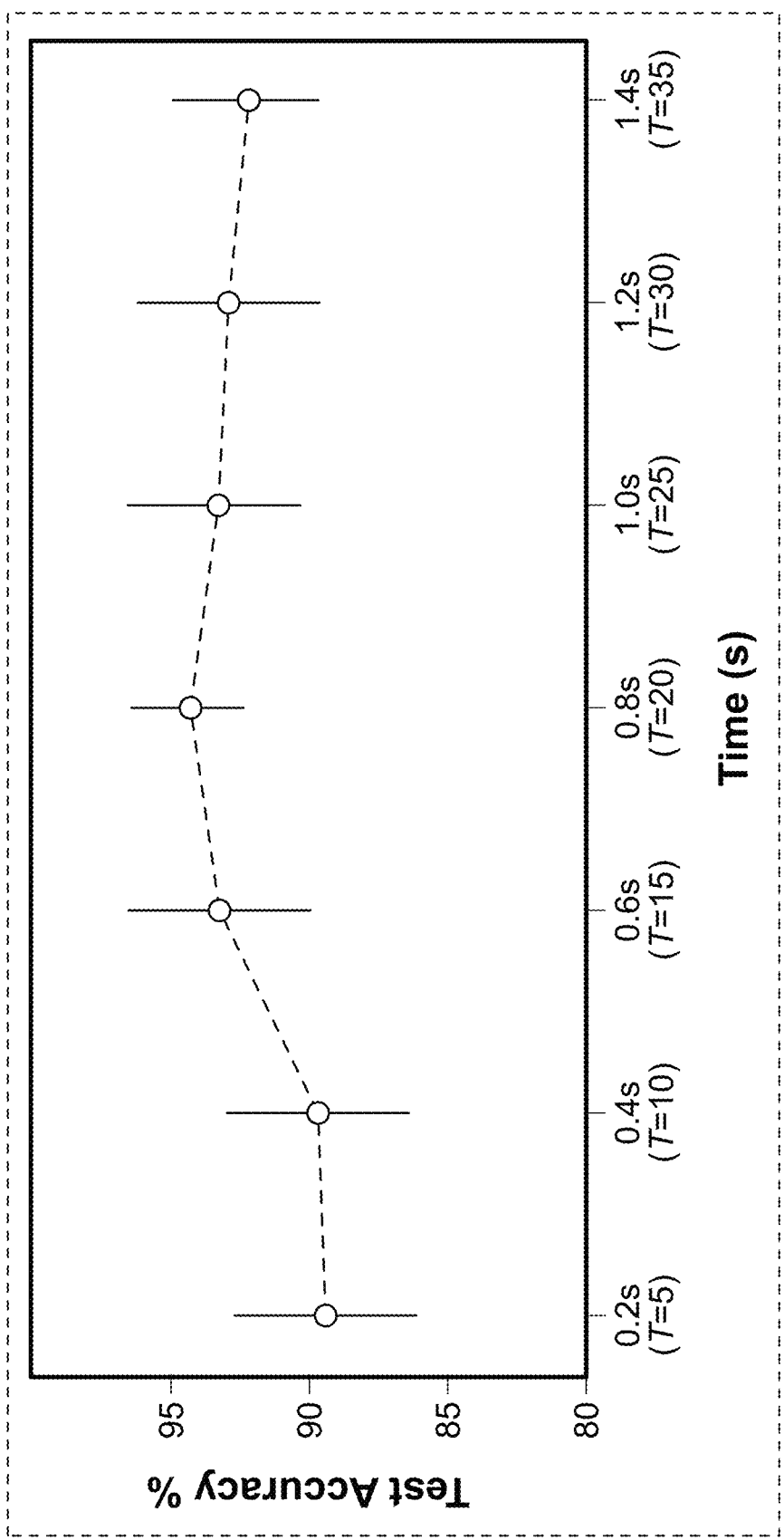
FIG. 13 graphically illustrates the test classification accuracy (circular marker) with the standard deviation (vertical line segment) for different T values.

The window length T is a hyper-parameter that determines the number of consecutive frames with maximum muscle activation for the temporal modeling component of the proposed examination. We evaluate different values of T (corresponding to various time duration in seconds) and provide the averaged 5-fold test accuracy as shown in FIG. 13. As shown in the figure the proposed system is relatively insensitive to various values of T. FIG. 13 graphically illustrates the test classification accuracy (circular marker) with the standard deviation (vertical line segment) for different T values. Because of the heterogeneity of the dataset collected in the wild, the duration of maximum muscle activation expressed by different subjects varies. Thus in our study, we choose T to be 0.83 seconds (20 frames). A smaller T is undesired because it would not be physiologically meaningful. In contrast, if T is too long, this increases the likelihood of added unwanted variations (e.g. oscillations due to adherence to instructions, noise) could lead to reduced predictive accuracy. FIG. 13 displays how the test accuracy changes with different window durations in seconds Prototype Implementation Detail We developed a prototype that integrated the proposed algorithm and a GUI to allow users to interact with the framework in real-time. Because our experiments demonstrated that near-mouth region contains more discriminant information than full face, the implementation concentrated on facial weakness detection only using near-mouth region. The layout of the GUI is shown on FIG. 4(B). The subject 401 can start, end, and retake the examination using the buttons on the top of the prototype. Below is an instruction text window 408 to display instructions, warning messages, and test results. When taking the test, the user can see the live stream from the camera with the facial landmarks and head pose detected. The head pose estimation ensures that the subject is able to face the camera directly with full face in view. The instruction shown on the text window guides the subject throughout the test, e.g., "to show a big smile and hold for the number of n seconds". Referring to FIG. 4(B), on the right side of the prototype, the mouth reference that is used to compute the optical now and the optical now estimation result from the current frame are displayed, which guarantee that the facial movement detector is able to locate the interested video segment successfully. When the examination is finished, the classification result shows up on test result area to inform the user, which is located at FIG. 4(B) on the right bottom of the prototype.

Additional Examples

Example 1. A system for analyzing facial weakness for predicting presence of one or more neurological deficits. The system may comprise: a camera; one or more memory devices configured to store instructions; and one or more processors. The processors may be configured to execute the instructions to: extract the facial landmarks from a video feed received from said camera; perform landmarks and intensity normalization that removes translation, rotation, and scaling variations from said extracted facial landmarks; detect facial movement by employing an optical flow method to measure the face movement intensity and locate a target video segment where a smile configuration is evident to obtain desired a video segment; extract shape features and appearance-based features from target frames inside said desired video segment, wherein said shape features and appearance-based features are high-dimensional; project said high-dimensional shape features and appearance-based features onto a low-dimensional subspace; classify the input video using said low-dimensional representation of shape features and appearance-based features via a recurrent neural network; and in response to said classification, predict a presence of one or more neurological deficits and transmit said predication to one or more secondary source devices.

Example 2. The system of example 1, wherein said one or more secondary source devices include one or more of any one of the following: one or more local memory devices; one or more remote memory devices; or one or more display or graphical user interface devices.

Example 3. The system of example 1 (as well as subject matter in whole or in part of example 2), wherein the system is a smart phone, tablet, laptop, desktop, smart mirror, or mobile device.

Example 4. The system of example 1 (as well as subject matter of one or more of any combination of examples 2-3, in whole or in part), wherein the instructions include a set of machine learning algorithms.

Example 5. The system of example 1 (as well as subject matter of one or more of any combination of examples 2-4, in whole or in part), wherein the one or more neurological deficits include at least one of asymmetric smile, asymmetric eyebrow raise, nystagmus, or stroke information including type of stroke and location of stroke.

Example 6. The system of example 5, wherein the asymmetric smile include left facial weakness (left) or right facial weakness (right).

Example 7. The system of example 1 (as well as subject matter of one or more of any combination of examples 2-5, in whole or in part), wherein facial landmarks include face and eye positions.

Example 8. The system of example 1 (as well as subject matter of one or more of any combination of examples 2-7, in whole or in part), wherein said shape-based features include facial landmarks and said appearance-based features include histogram of oriented gradient (HoG) features.

Example 9. The system of example 1 (as well as subject matter of one or more of any combination of examples 2-8, in whole or in part), wherein said one or more processors are configured to executed instructions to: apply a rigid body estimation method to estimate said translation, rotation, and scaling.

Example 10. The system of example 1 (as well as subject matter of one or more of any combination of examples 2-9, in whole or in part), wherein said optical flow method identifies a full smile activation.

Example 11. The system of example 1 (as well as subject matter of one or more of any combination of examples 2-10, in whole or in part), wherein said one or more processors are configured to executed instructions to: model the pathological meaningful shape and appearance variation on an neurologist-verified image dataset that is independent of the video dataset in a supervised-learning fashion.

Example 12. The system of example 1 (as well as subject matter of one or more of any combination of examples 2-11, in whole or in part), wherein said one or more processors are configured to executed instructions to: apply a temporal modeling algorithm to predict the label y for the feature sequence $\{\bar{x}_t\}_{t=1}^T$ via a recurrent neural network (RNN) based approach.

Example 13. The system of claim 12, wherein said recurrent neural network (RNN) based approach is bi-directional long short-term memory network (Bi-LSTM).

Example 14. A computer-implemented method for analyzing facial weakness for predicting presence of one or more neurological deficits. The method may comprise: extracting the facial landmarks from a video feed received from a camera; performing landmarks and intensity normalization that removes translation, rotation, and scaling variations from said extracted facial landmarks; detecting facial movement by employing an optical flow method to measure the face movement intensity and locate a target video segment where a smile configuration is evident to obtain desired a video segment; extracting shape features and appearance-based features from target frames inside said desired video segment, wherein said shape features and appearance-based features are high-dimensional; projecting said high-dimensional shape features and appearance-based features onto a low-dimensional subspace; classifying the input video using said low-dimensional representation of shape features and appearance-based features via a recurrent neural network; and in response to said classification, predicting a presence of one or more neurological deficits, and transmitting said predication to one or more secondary source devices.

Example 15. The method of example 14, wherein said one or more secondary source devices include one or more of any one of the following: one or more local memory devices; one or more remote memory devices; or one or more display or graphical user interface devices.

Example 16. The method of example 14 (as well as subject matter in whole or in part of example 15), wherein a smart phone, tablet, laptop, desktop, smart mirror, or mobile device is used to perform the method.

Example 17. The method of example 14 (as well as subject matter of one or more of any combination of examples 15-16, in whole or in part), further comprising one or more processors configured to execute instructions to perform the method and wherein the instructions include a set of machine learning algorithms.

Example 18. The method of example 14 (as well as subject matter of one or more of any combination of examples 15-17, in whole or in part), wherein the one or more neurological deficits include at least one of asymmetric smile, asymmetric eyebrow raise, nystagmus, or stroke information including type of stroke and location of stroke.

Example 19. The method of example 18, wherein the asymmetric smile include left facial weakness (left) or right facial weakness (right).

Example 20. The method of example 14 (as well as subject matter of one or more of any combination of examples 15-19, in whole or in part), wherein facial landmarks include face and eye positions.

Example 21. The method of example 14 (as well as subject matter of one or more of any combination of examples 15-20, in whole or in part), wherein said shape-based features include facial landmarks and said appearance-based features include histogram of oriented gradient (HoG) features.

Example 22. The method of example 14 (as well as subject matter of one or more of any combination of examples 15-21, in whole or in part), further comprising: applying a rigid body estimation method to estimate said translation, rotation, and scaling.

Example 23. The method of example 14 (as well as subject matter of one or more of any combination of examples 15-22, in whole or in part), wherein said optical flow method identifies a full smile activation.

Example 24. The method of example 14 (as well as subject matter of one or more of any combination of examples 15-23, in whole or in part), further comprising: modeling the pathological meaningful shape and appearance variation on an neurologist-verified image dataset that is independent of the video dataset in a supervised-learning fashion.

Example 25. The method of example 14 (as well as subject matter of one or more of any combination of examples 15-24, in whole or in part), further comprising: applying a temporal modeling algorithm to predict the label y for the feature sequence $\{\overline{x}_t\}_{t=1}^T$ via a recurrent neural network (RNN) based approach.

Example 26. The method of claim 25, wherein said recurrent neural network (RNN) based approach is bi-directional long short-term memory network (Bi-LSTM).

Example 27. A non-transitory computer-readable medium storing instructions that, when executed by one or more processors, cause the one or more processors to perform operations for analyzing facial weakness for predicting presence of one or more neurological deficits. The non-transitory computer-readable medium may comprise: extracting the facial landmarks from a video feed received from a camera; performing landmarks and intensity normalization that removes translation, rotation, and scaling variations from said extracted facial landmarks; detecting facial movement by employing an optical flow method to measure the face movement intensity and locate a target video segment where a smile configuration is evident to obtain desired a video segment; extracting shape features and appearance-based features from target frames inside said desired video segment, wherein said shape features and appearance-based features are high-dimensional; projecting said high-dimensional shape features and appearance-based features onto a low-dimensional subspace; classifying the input video using said low-dimensional representation of shape features and appearance-based features via a recurrent neural network; and in response to said classification, predicting a presence of one or more neurological deficits, and transmitting said predication to one or more secondary source devices.

Example 28. The non-transitory computer-readable medium of example 27, wherein said one or more secondary source devices include one or more of any one of the following: one or more local memory devices; one or more remote memory devices; or one or more display or graphical user interface devices.

Example 29. The non-transitory computer-readable medium of example 27 (as well as subject matter in whole or in part of example 28), wherein a smart phone, tablet, laptop, desktop, smart mirror, or mobile device is used to perform the method.

Example 30. The non-transitory computer-readable medium of example 27 (as well as subject matter of one or more of any combination of examples 28-29, in whole or in part), further comprising one or more processors configured to execute instructions to perform the method and wherein the instructions include a set of machine learning algorithms.

Example 31. The non-transitory computer-readable medium of example 27 (as well as subject matter of one or more of any combination of examples 28-30, in whole or in part), wherein the one or more neurological deficits include at least one of asymmetric smile, asymmetric eyebrow raise, nystagmus, or stroke information including type of stroke and location of stroke.

Example 32. The non-transitory computer-readable medium of example 31, wherein the asymmetric smile include left facial weakness (left) or right facial weakness (right).

Example 33. The non-transitory computer-readable medium of example 27 (as well as subject matter of one or more of any combination of examples 28-32, in whole or in part), wherein facial landmarks include face and eye positions.

Example 34. The non-transitory computer-readable medium of example 27 (as well as subject matter of one or more of any combination of examples 28-33, in whole or in part), wherein said shape-based features include facial landmarks and said appearance-based features include histogram of oriented gradient (HoG) features.

Example 35. The non-transitory computer-readable medium of example 27 (as well as subject matter of one or more of any combination of examples 28-34, in whole or in part), further comprising: applying a rigid body estimation method to estimate said translation, rotation, and scaling.

Example 36. The non-transitory computer-readable medium of example 27 (as well as subject matter of one or more of any combination of examples 28-35, in whole or in part), wherein said optical flow method identifies a full smile activation.

Example 37. The non-transitory computer-readable medium of example 27 (as well as subject matter of one or more of any combination of examples 28-36, in whole or in part), further comprising: modeling the pathological meaningful shape and appearance variation on an neurologist-verified image dataset that is independent of the video dataset in a supervised-learning fashion.

Example 38. The non-transitory computer-readable medium of example 27 (as well as subject matter of one or more of any combination of examples 28-37, in whole or in part), further comprising: applying a temporal modeling algorithm to predict the label y for the feature sequence $\{\overline{x}_t\}_{t=1}^T$ via a recurrent neural network (RNN) based approach.

Example 39. The non-transitory computer-readable medium of claim 38, wherein said recurrent neural network (RNN) based approach is bi-directional long short-term memory network (Bi-LSTM).

Example 40. A system configured to perform the method of any one or more of Examples 1-13.

Example 41. A computer program product configured to perform the method of any one or more of Examples 1-13.

Example 42. The method of using any of the elements, components, devices, computer program product and/or systems, or their sub-components, provided in any one or more of examples 14-26, in whole or in part.

Example 43. The method of manufacturing any of the elements, components, devices, computer program product and/or systems, or their sub-components, provided in any one or more of examples 14-26, in whole or in part.

REFERENCES

The devices, systems, apparatuses, modules, compositions, materials, compositions, computer program products, non-transitory computer readable medium, and methods of various embodiments of the invention disclosed herein may utilize aspects (such as devices, apparatuses, modules, systems, compositions, materials, compositions, computer program products, non-transitory computer readable medium, and methods) disclosed in the following references, applications, publications and patents and which are hereby incorporated by reference herein in their entirety (and which are not admitted to be prior art with respect to the present invention by inclusion in this section).

[1] D. DoPatel and K. Levin, "Bell palsy: Clinical examination and management," Cleveland Clin. J Med., vol. 82, no. 7, pp. 419, 2015.

[2] K. Yew and E. Cheng, "Acute stroke diagnosis," Amer. Fan. Physician, vol. 80, no. 1, pp. 33-40, 2009.

[3] A. Nor et al, "Agreement between ambulance paramedic- and physician-recorded neurological signs with face arm speech test (fast) in acute stroke patients," Stroke, vol. 35, no. 6, pp. 1355-1359, 2004.

[4] M. Hansen et al., "Interobsserver variation in the evaluation of neurological signs: Observer dependent factors," Acta Neurologica Scandinavica, vol. 90, no. 3, pp. 145-149, 1994.

[5] W. Powers et al, "2015 american heart association/american stroke association focused update of the 2013 guidelines for the early management of patients with acute ischemic stroke regarding endovascular treatment," Stroke, vol 46, no. 10, pp. 3020-3035, 2015.

[6] S. Reitzen et al., "Significance and reliability of the House-Brackmann grading system for regional facial nerve function," Otolaryngol-Head Neck Surg., vol. 140, no. 2, pp. 154-158, 2009.

[7] L Mosley et al., "The impact of ambulance practice on acute stroke care," Stroke, vol. 38, no. 10, pp. 2765-2770, 2007.

[8] H. Adams, Jr. et al, "Guidelines for the early management of adults with ischemic stroke," Stroke, vol. 38, no. 5, pp. 1655-1711, 2007.

[9] N. Glober et al., "Acute stroke: Current evidence-based recommendations for prehospital care," Western J. Energ. Med., vol. 17, no. 2, pp. 104, 2016.

[10] R. Sacco, "Neurology: Challenges, opportunities, and the way forward," Neurol., vol. 93, no. 21, pp. 911-918, 2019.

[11] T. Moulin et a., "Telemedicine in stroke: Potentials, limitations and ongoing issues," in Proc. Adv. Telemed.: Appl. Various Med. DisciplinesGeogr. Regions. IntechOpen, 2011, pp. 3-28.

[12] Y. LeCun et al., "Deep Learning," Nature, vol 521, no. 7553, pp. 436-444, 2015.

[13] J. Thevenot et at, "A survey on computer vision for assistive medical diagnosis from faces," IEEE J. Biomed. Health Inform., vol. 22, no. 5, pp. 1497-1511, September 2018.

[14] C. Linstrom et al., "Facial-motion analysis with a video and computer system: A preliminary report," Otol Neurotol., vol. 21, no. 1, pp. 123-129, 2000.

[15] B. Ko, "A brief review of facial emotion recognition based on visual information," Sensors, vol. 18, no. 2, pp. 401-420, 2018.

[16] A. Song et al, "Assessment for facial nerve paralysis based on facial asymmetry," Australas. Phys. Eng. Sci. Med., vol. 40, no. 4, pp. 851-860, 2017.

[17] Y, Zhuang et al., "Pathological facial weakness detection using computational image analysis," in Proc. IEEE 15th Int. Synp. Biomed. Imag., 2018, pp. 261-264.

[18] Z. Guo et al, "An unobtrusive computerized assessment framework for unilateral peripheral facial paralysis," IEEE J. Biomed. Health Inform., vol 22, no. 3, pp. 835-841, May 2018.

[19] Y. Zhuang et al., "Facial weakness analysis and quantification of static images," IEEE J. Biomed. Health Informat., vol. 24, no. 8, pp. 2260-2267, August 2020.

[20] Z. Guo et at, "Deep assessment process: Objective assessment process for unilateral peripheral facial paralysis via deep convolutional neural network," in Proc. IEEE 14th Int. Symp. Biomed. Imag., 2017, pp. 135-138.

[21]). Haase et al., "Automated and objective action coding of facial expressions in patients with acute facial palsy," Eur. Arch. Oto-Rhino-Laryngol., vol. 272, no. 5, pp. 1259-1267, 2015.

[22] L. Modersohn and J. Denzlcr, "Facial paresis index prediction by exploiting active appearance models for compact discriminative features," in Proc. VISIGRAPP (4: VISAPIP), 2016, pp. 271-278.

[23] H. Kim et al, "A smartphone-based automatic diagnosis system for facial nerve palsy," Sensors, vol. 15, no. 10, pp. 26756-26768, 2015.

[24] T. Wang et al, "Automatic evaluation of the degree of facial nerve paralysis," Multinedia Tools Appl., vol. 75, no. 19, pp. 11893-11908, 2016.

[25] A. Gaber et al, "Quantifying facial paralysis using the kinect v2," in Proc. 37th Annu. Int. Conf. IEEE Eng. Med. Biol. Soc, 2015, pp. 2497-2501.

[26] S. He, J. J. Soraghan, B. F. O'Reilly and D. Xing, "Quantitative analysis of facial paralysis using local binary patterns in biomedical videos," IEEE Trans. Biomed. Eng., vol. 56, no. 7, pp. 1864-1870, July 2009.

[27] S. He et at, "Biomedical image sequence analysis with application to automatic quantitative assessment of facial paralysis," *EURASIP J. Image Video Process.*, vol. 2007, pp. 1-11, 2007.

[28] P. Li et al., "A two-stage method for assessing facial paralysis severity by fusing multiple classifiers," in *Proc. Chin. Conf. Biometric Recognit.*, 2019, pp. 231-239.

[29] Y. Zhuang et al., "F-dit-v: An automated video classification tool for facial weakness detection," in *Proc. IEEE EMBS Int. Conf. Biomed. Health Inform.*, 2019, pp. 1-4.

[30] P. Xu et al., "Automatic evaluation of facial nerve paralysis by dual-path lstm with deep differentiated network," *Neurocomput.* vol. 388, pp. 70-77, 2020, doi: 10.1016/j.neucom.2020.01.014.

[31] G. Storey et al., "3dpalsynet: A facial palsy grading and motion recognition framework using fully 3 d convolutional neural networks," *IEEE Access*, vol. 7, pp. 121655-121664, 2019.

[32] A. Bandini et al, "Automatic detection of amyotrophic lateralsclerosis (als) from video-based analysis of facial movements: Speech and non-speech tasks," in *Proc. 13th IEEE Int. Conf. Automat. Face Gesture Recognit.*, 2018, pp. 150-157.

[33] M. Alagha et al., "Reproducibility of the dynamics of facial expressions in unilateral facial palsy," *Int. J. Oral Maxillofac. Surg.*, vol. 47, no. 2, pp. 268-275, 2018.

[34] P. Desrosiers ef al., "Analyzing of facial paralysis by shape analysis of 3d face sequences," *Image Vis. Conput.*, vol. 67, pp. 67-88, 2017.

[35] P. Felzenszwalb et al., "Object detection with discriminatively trained part-based models," *IEEE Trans. Pattern Anal. Mach. Intell*, vol. 32, no. 9, pp. 1627-1645, September 2010.

[36] J. Gower, "Generalized procrustes analysis," *Psychometrika*, vol. 40, no. 1, pp. 33-51, 1975.

[37] M. Irani, "Multi-frame optical flow estimation using subspace constraints," in *Proc. 7th IEEE Int. Conf. Comput. Vis.*, 1999, pp. 626-633.

[38] H. Abdi and L. Williams, "Principal component analysis," *Wiley Interdis-cipl. Rev.: Comput. Stat.*, vol. 2, no. 4, pp. 433-459, 2010.

[39] W. Wang et al, "Penalized fisher discriminant analysis and its application to image-based morphometry." *Pattern Recognit. Lett.*, vol. 32, no. 15, pp. 2128-2135, 2011.

[40] L Goodfellow et al, *Deep Learning*, Cambridge, MA, USA: MIT press Cambridge, vol. 1, 2016.

[41] H. Adams et al, "Baseline nih stroke scale score strongly predicts outcome after stroke: A report of the trial of org 10172 in acute stroke treatment (toast)," *Neurology*, vol. 53, no. 1, pp. 126-126, 1999.

[42] V. Kazemi and J. Sullivan, "One millisecond face alignment with an ensemble of regression trees," in *Proc. IEEE Conf. Comput. Vis. Pattern Recognit.*, 2014, pp. 1867-1874.

[43] G. Chrysos et al, "A comprehensive performance evaluation of deformable face tracking in-the-wild," *Int. J. Conput. Vis.* vol. 126, no. 2-4, pp. 198-232, 2018.

[44] J. Donahue et al, "Long-term recurrent convolutional networks for visual recognition and description," in *Proc. IEEE Conf. Conput. Vis. Pattern Recognit*, 2015, pp. 2625-2634.

[45] C. Ma et al., "Ts-lstm and temporal-inception: Exploiting spatiotemporal dynamics for activity recognition," *Signal Process.: Image Commun.*, vol. 71, pp. 76-87, 2019.

[46] T. Dietterich, "Approximate statistical tests for comparing supervised classification learning algorithms," *Neural Comput.*, vol. 10, no. 7, pp. 1895-1923, 1998.

[47] S. Raschka, "Mixtend: Providing machine learning and data science utilities and extensions to python's scientific computing stack," *J. Open Sour. Softw.*, vol. 3, no. 24, pp. 638-640, 2018.

[48] S. Nag et al, "Facial micro-expression spotting and recognition using time contrasted feature with visual memory," in *Proc. ICASSP IEEE Int. Conf Acoust., Speech Signal Process.*, 2019, pp. 2022-2026.

[49] N. Maheswaranathan et al., "Reverse engineering recurrent networks for sentiment classification reveals line attractor dynamics," in *Proc. Adv. Neural Inf. Process. Syst.*, 2019, pp. 15696-15705.

[50] Logitech, "C920 technical specifications," January 2013. [Online]. Available: https://support.logi.com/hc/en-us/articles/360023307294-C920-Technical-Specifications

[51] H. Greenspan, B. van Ginneken and R. M. Summers, "Guest editorial deep learning in medical imaging: Overview and future promise of an exciting new technique," *IEEE Trans. Med. Imag.*, vol. 35, no. 5, pp. 1153-1159, May 2016.

[52] A. Esteva et al., "A guide to deep learning in healthcare," *Nat. Med.*, vol. 25, no. 1, pp. 24-29, 2019.

[53] S. Li and W. Deng, "Deep facial expression recognition: A. survey," *IEEE Trans. Affect. Comput.*, to be published, doi: 10.1109/TAFFC.2020.2981446.

[54] K. Simonyan and A. Zisserman, "Two-stream convolutional networks for action recognition in videos," in *Proc. Adv. Neural Inf. Process. Syst.*, 2014, pp. 568-576.

[55] Y. Zhuang et al., "Video-Based Facial Weakness Analysis," IEEE Transactions on Biomedical Engineering, Supplemental, vol. 68, no. 9, (https://doi.org/10.1109/TBME.2021.3049739) pp. 9-10, September 2021.

Additional References

The devices, systems, apparatuses, modules, compositions, materials, compositions, computer program products, non-transitory computer readable medium, and methods of various embodiments of the invention disclosed herein may utilize aspects (such as devices, apparatuses, modules, systems, compositions, materials, compositions, computer program products, non-transitory computer readable medium, and methods) disclosed in the following references, applications, publications and patents and which are hereby incorporated by reference herein in their entirety (and which are not admitted to be prior art with respect to the present invention by inclusion in this section).

A. U.S. Patent Application Publication No. US 2017/0046569 A1, Krishna Rao, et al., "System and Method for Predicting Neurological Disorders", Feb. 16, 2017.

B. U.S. Patent Application Publication No. US 2011/0218253 A1, Lange, et al., "Imaging-Based Identification of a Neurological Disease or a Neurological Disorder", Sep. 8, 2011.

C. U.S. Patent Application Publication No. US 2015/0112232 A1, Quatieri, et al., "Using Correlation Structure of Speech Dynamics to Detect Neurological Changes", Apr. 23, 2015.

D. U.S. Utility patent application Ser. No. 15/733,244, entitled "SYSTEM AND METHOD FOR AUTOMATED DETECTION OF NEUROLOGICAL DEFICITS", filed Jun. 16, 2020.

E. International Patent Application Serial No. PCT/US2019/014605, entitled "SYSTEM AND METHOD FOR AUTOMATED DETECTION OF NEUROLOGICAL DEFICITS", filed Jan. 22, 2019; Publication No. WO 2019/144141, Jul. 25, 2019.

F. U.S. Utility patent application Ser. No. 14/910,890, entitled "TECHNIQUES FACILITATING MOBILE TELEMEDICINE FOR STROKE PATIENTS", filed Feb. 8, 2016; U.S. Pat. No. 10,846,370, issued Nov. 24, 2020.

G. International Patent Application Serial No. PCT/US2014/051664, entitled "TECHNIQUES FACILITATING MOBILE TELEMEDICINE FOR STROKE PATIENTS", filed Aug. 19, 2014; Publication No. WO 2015/026808, Feb. 26, 2015.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A system for analyzing facial weakness for predicting presence of one or more neurological deficits, comprising:
   a camera;
   one or more memory devices configured to store instructions; and
   one or more processors are configured to execute the instructions to:
      extract the facial landmarks from a video feed received from said camera;
      perform landmarks and intensity normalization that removes translation, rotation, and scaling variations from said extracted facial landmarks;
      detect facial movement by employing an optical flow method to measure the face movement intensity and locate a target video segment where a smile configuration is evident to obtain desired a video segment;
      extract shape features and appearance-based features from target frames inside said desired video segment, wherein said shape features and appearance-based features are high-dimensional;
      project said high-dimensional shape features and appearance-based features onto a low-dimensional subspace;
      classify the input video using said low-dimensional representation of shape features and appearance-based features via a recurrent neural network; and
      in response to said classification, predict a presence of one or more neurological deficits and transmit said predication to one or more secondary source devices.

2. The system of claim 1, wherein said one or more secondary source devices include one or more of any one of the following:
   one or more local memory devices;
   one or more remote memory devices; or
   one or more display or graphical user interface devices.

3. The system of claim 1, wherein the system is a smart phone, tablet, laptop, desktop, smart mirror, or mobile device.

4. The system of claim 1, wherein the instructions include a set of machine learning algorithms.

5. The system of claim 1, wherein the one or more neurological deficits include at least one of asymmetric smile, asymmetric eyebrow raise, nystagmus, or stroke information including type of stroke and location of stroke.

6. The system of claim 5, wherein the asymmetric smile include left facial weakness (left) or right facial weakness (right).

7. The system of claim 1, wherein facial landmarks include face and eye positions.

8. The system of claim 1, wherein said shape-based features include facial landmarks and said appearance-based features include histogram of oriented gradient (HoG) features.

9. The system of claim 1, wherein said one or more processors are configured to executed instructions to:
   apply a rigid body estimation method to estimate said translation, rotation, and scaling.

10. The system of claim 1, wherein said optical flow method identifies a full smile activation.

11. The system of claim 1, wherein said one or more processors are configured to executed instructions to:
   model the pathological meaningful shape and appearance variation on an neurologist-verified image dataset that is independent of the video dataset in a supervised-learning fashion.

12. The system of claim 1, wherein said one or more processors are configured to executed instructions to:
   apply a temporal modeling algorithm to predict the label $\hat{y}$ for the feature sequence $\{\overline{x}_t\}_{t=1}^T$ via a recurrent neural network (RNN) based approach.

13. The system of claim 12, wherein said recurrent neural network (RNN) based approach is bi-directional long short-term memory network (Bi-LSTM).

14. A computer-implemented method for analyzing facial weakness for predicting presence of one or more neurological deficits, said method comprising:
   extracting the facial landmarks from a video feed received from a camera;
   performing landmarks and intensity normalization that removes translation, rotation, and scaling variations from said extracted facial landmarks;
   detecting facial movement by employing an optical flow method to measure the face movement intensity and locate a target video segment where a smile configuration is evident to obtain desired a video segment;
   extracting shape features and appearance-based features from target frames inside said desired video segment, wherein said shape features and appearance-based features are high-dimensional;
   projecting said high-dimensional shape features and appearance-based features onto a low-dimensional subspace;
   classifying the input video using said low-dimensional representation of shape features and appearance-based features via a recurrent neural network; and
   in response to said classification, predicting a presence of one or more neurological deficits, and transmitting said predication to one or more secondary source devices.

15. The method of claim 14, wherein said one or more secondary source devices include one or more of any one of the following:
   one or more local memory devices;
   one or more remote memory devices; or
   one or more display or graphical user interface devices.

16. The method of claim 14, wherein a smart phone, tablet, laptop, desktop, smart mirror, or mobile device is used to perform the method.

17. The method of claim 14, further comprising one or more processors configured to execute instructions to perform the method and wherein the instructions include a set of machine learning algorithms.

18. The method of claim 14, wherein the one or more neurological deficits include at least one of asymmetric smile, asymmetric eyebrow raise, nystagmus, or stroke information including type of stroke and location of stroke.

19. The method of claim 18, wherein the asymmetric smile include left facial weakness (left) or right facial weakness (right).

20. The method of claim 14, wherein facial landmarks include face and eye positions.

21. The method of claim 14, wherein said shape-based features include facial landmarks and said appearance-based features include histogram of oriented gradient (HoG) features.

22. The method of claim 14, further comprising:
   applying a rigid body estimation method to estimate said translation, rotation, and scaling.

23. The method of claim 14, wherein said optical flow method identifies a full smile activation.

24. The method of claim 14, further comprising:
   modeling the pathological meaningful shape and appearance variation on an neurologist-verified image dataset that is independent of the video dataset in a supervised-learning fashion.

25. The method of claim 14, further comprising:
   applying a temporal modeling algorithm to predict the label $\hat{y}$ for the feature sequence $\{\overline{x}_t\}_{t=1}^T$ via a recurrent neural network (RNN) based approach.

26. The method of claim 25, wherein said recurrent neural network (RNN) based approach is bi-directional long short-term memory network (Bi-LSTM).

27. A non-transitory computer-readable medium storing instructions that, when executed by one or more processors, cause the one or more processors to perform operations for analyzing facial weakness for predicting presence of one or more neurological deficits, comprising:
   extracting the facial landmarks from a video feed received from a camera;
   performing landmarks and intensity normalization that removes translation, rotation, and scaling variations from said extracted facial landmarks;
   detecting facial movement by employing an optical flow method to measure the face movement intensity and locate a target video segment where a smile configuration is evident to obtain desired a video segment;
   extracting shape features and appearance-based features from target frames inside said desired video segment, wherein said shape features and appearance-based features are high-dimensional;
   projecting said high-dimensional shape features and appearance-based features onto a low-dimensional subspace;
   classifying the input video using said low-dimensional representation of shape features and appearance-based features via a recurrent neural network; and
   in response to said classification, predicting a presence of one or more neurological deficits, and transmitting said predication to one or more secondary source devices.

28. The non-transitory computer-readable medium of claim 27, wherein said one or more secondary source devices include one or more of any one of the following:
   one or more local memory devices;
   one or more remote memory devices; or
   one or more display or graphical user interface devices.

29. The non-transitory computer-readable medium of claim 27, wherein a smart phone, tablet, laptop, desktop, smart mirror, or mobile device is used to perform the method.

30. The non-transitory computer-readable medium of claim 27, further comprising one or more processors configured to execute instructions to perform the method and wherein the instructions include a set of machine learning algorithms.

31. The non-transitory computer-readable medium of claim 27, wherein the one or more neurological deficits include at least one of asymmetric smile, asymmetric eyebrow raise, nystagmus, or stroke information including type of stroke and location of stroke.

32. The non-transitory computer-readable medium of claim 31, wherein the asymmetric smile include left facial weakness (left) or right facial weakness (right).

33. The non-transitory computer-readable medium of claim 27, wherein facial landmarks include face and eye positions.

34. The non-transitory computer-readable medium of claim 27, wherein said shape-based features include facial landmarks and said appearance-based features include histogram of oriented gradient (HoG) features.

35. The non-transitory computer-readable medium of claim 27, further comprising:
applying a rigid body estimation method to estimate said translation, rotation, and scaling.

36. The non-transitory computer-readable medium of claim 27, wherein said optical flow method identifies a full smile activation.

37. The non-transitory computer-readable medium of claim 27, further comprising:
modeling the pathological meaningful shape and appearance variation on an neurologist-verified image dataset that is independent of the video dataset in a supervised-learning fashion.

38. The non-transitory computer-readable medium of claim 27, further comprising:
applying a temporal modeling algorithm to predict the label $\hat{y}$ for the feature sequence $\{\overline{x}_t\}_{t=1}^{T}$ via a recurrent neural network (RNN) based approach.

39. The non-transitory computer-readable medium of claim 38, wherein said recurrent neural network (RNN) based approach is bi-directional long short-term memory network (Bi-LSTM).

\* \* \* \* \*